United States Patent
Bowling

(10) Patent No.: US 9,993,309 B2
(45) Date of Patent: Jun. 12, 2018

(54) FORCE/TORQUE TRANSDUCER AND METHOD OF OPERATING THE SAME

(71) Applicant: Stryker Corporation, Kalamazoo, MI (US)

(72) Inventor: David Gene Bowling, Los Ranchos de Albuquerque, NM (US)

(73) Assignee: STRYKER CORPORATION, Kalamazoo, MI (US)

(*) Notice: Subject to any disclaimer, the term of this patent is extended or adjusted under 35 U.S.C. 154(b) by 0 days. days.

(21) Appl. No.: 15/014,739

(22) Filed: Feb. 3, 2016

(65) Prior Publication Data

US 2016/0220319 A1    Aug. 4, 2016

Related U.S. Application Data

(60) Provisional application No. 62/111,257, filed on Feb. 3, 2015.

(51) Int. Cl.
*G01L 5/16* (2006.01)
*A61B 34/30* (2016.01)
(Continued)

(52) U.S. Cl.
CPC .............. *A61B 34/30* (2016.02); *A61B 90/06* (2016.02); *B25J 13/085* (2013.01);
(Continued)

(58) Field of Classification Search
CPC ....................................................... G01L 5/161
See application file for complete search history.

(56) References Cited

U.S. PATENT DOCUMENTS 3,205,706 A   9/1965 Tracy
3,315,203 A   4/1967 Jacobson
(Continued)

FOREIGN PATENT DOCUMENTS

EP   0160282 A2   11/1985
EP   0160282 B1   11/1985
(Continued)

OTHER PUBLICATIONS

English language abstract not available for JP60238760. Abstract of corresponding document: EP0160282 (A2) extracted from espacenet.com database on Oct. 28, 2016, 20 pages.
(Continued)

*Primary Examiner* — Harshad R Patel
*Assistant Examiner* — Tran M Tran
(74) *Attorney, Agent, or Firm* — Howard & Howard Attorneys PLLC

(57) ABSTRACT

A force/torque transducer comprises a first member, a second member for receiving a load, and load cells connecting the first and second members. The load cells include sensors for measuring physical deformation of the load cells. Sensor measurements are convertible into force/torque measurements using a transformation matrix configured with M rows and N columns. M and N are respectively defined by a number of degrees of freedom monitored by the transducer and a number of load cells employed by the transducer, or vice-versa. Each row or column that corresponds to each load cell has values relating to that one load cell. Each row or column that corresponds to each degree of freedom has values relating to that one degree of freedom. A sum of the values in each row or column corresponding to each degree of freedom is substantially equal to zero.

18 Claims, 23 Drawing Sheets

(51) Int. Cl.
*A61B 90/00* (2016.01)
*G01L 3/10* (2006.01)
*B25J 13/08* (2006.01)
*G01L 1/22* (2006.01)

(52) U.S. Cl.
CPC ............ *G01L 1/2206* (2013.01); *G01L 3/108* (2013.01); *G01L 5/16* (2013.01); *G01L 5/162* (2013.01); *A61B 2090/065* (2016.02); *A61B 2090/066* (2016.02)

(56) References Cited

U.S. PATENT DOCUMENTS

| | | | |
|---|---|---|---|
| 3,422,445 A | 1/1969 | Jacobson | |
| 3,433,064 A | 3/1969 | Jacobson | |
| 3,636,760 A | 1/1972 | Shoberg | |
| 4,094,192 A | 6/1978 | Watson et al. | |
| 4,398,429 A | 8/1983 | Cook et al. | |
| 4,442,718 A * | 4/1984 | Komarova | G01B 5/0014 73/766 |
| 4,488,441 A | 12/1984 | Ramming | |
| 4,577,513 A * | 3/1986 | Harwood | G01L 3/1457 414/730 |
| 4,620,436 A * | 11/1986 | Hirabayashi | B25J 9/1692 73/1.15 |
| 4,821,582 A * | 4/1989 | Meyer | G01L 5/161 73/146 |
| 4,823,618 A | 4/1989 | Ramming | |
| 4,849,730 A * | 7/1989 | Izumi | G01L 1/18 338/2 |
| 4,911,024 A | 3/1990 | McMaster | |
| 5,063,788 A | 11/1991 | Ch'Hayder et al. | |
| 5,222,398 A * | 6/1993 | O'Brien | G01L 1/2243 177/211 |
| 5,295,399 A * | 3/1994 | Grant | G01L 5/226 73/862.043 |
| 5,490,427 A | 2/1996 | Yee et al. | |
| 5,706,027 A * | 1/1998 | Hilton | B25J 13/02 345/156 |
| 5,837,946 A * | 11/1998 | Johnson | G01G 3/1404 177/136 |
| 5,889,214 A * | 3/1999 | Kang | G01L 5/161 73/862.043 |
| 6,105,438 A * | 8/2000 | Gieseke | G01L 5/16 73/862.042 |
| 6,253,626 B1 * | 7/2001 | Shoberg | G01L 5/161 73/775 |
| 6,269,702 B1 * | 8/2001 | Lambson | G01L 3/108 73/862.045 |
| 6,295,878 B1 * | 10/2001 | Berme | G01L 1/2206 73/862.044 |
| 6,382,012 B2 * | 5/2002 | Hara | G01L 25/00 73/1.15 |
| 6,694,828 B1 * | 2/2004 | Nicot | B62D 1/16 180/422 |
| 6,742,400 B2 * | 6/2004 | Yoon | G01M 1/10 73/862.043 |
| 6,769,312 B2 * | 8/2004 | Meyer | G01L 5/161 73/862.042 |
| 6,792,815 B2 * | 9/2004 | McDearmon | G01L 5/161 73/862.041 |
| 6,845,675 B2 | 1/2005 | Meyer et al. | |
| 6,871,552 B2 * | 3/2005 | Liu | G01L 5/161 73/862.041 |
| 6,915,709 B2 * | 7/2005 | Okada | G01L 5/165 73/862.041 |
| 7,121,147 B2 * | 10/2006 | Okada | G01L 5/165 73/760 |
| 7,360,456 B2 | 4/2008 | Morimoto | |
| 7,437,954 B2 | 10/2008 | Sakano | |
| 7,594,445 B2 * | 9/2009 | Hirabayashi | G01L 1/26 73/862.041 |
| 7,665,371 B2 * | 2/2010 | Mastinu | F16C 11/12 73/760 |
| 7,779,705 B2 * | 8/2010 | Mastinu | G01L 3/22 73/862.046 |
| 8,156,823 B2 * | 4/2012 | Kim | G01L 5/16 73/862.041 |
| 8,161,828 B1 * | 4/2012 | Clegg | G01L 3/1457 73/862.08 |
| 8,408,075 B2 | 4/2013 | Okada | |
| 8,621,939 B2 * | 1/2014 | Blumenkranz | G01L 1/246 606/1 |
| 8,627,730 B2 * | 1/2014 | Valov | G01L 3/1457 73/862.044 |
| 8,844,376 B2 * | 9/2014 | Siklos | G01L 5/223 73/862.042 |
| 8,904,883 B2 * | 12/2014 | Clegg | G01L 3/1457 73/862.08 |
| 8,943,902 B2 * | 2/2015 | Bosscher | G01L 5/226 73/862.041 |
| 8,984,962 B2 * | 3/2015 | Christmann | G01L 3/10 73/862.041 |
| 9,052,250 B1 * | 6/2015 | Parker | G01L 25/00 |
| 9,080,921 B2 * | 7/2015 | Okada | G01L 25/00 |
| 9,274,014 B2 * | 3/2016 | Janik | G01L 5/16 |
| 9,274,015 B2 * | 3/2016 | Schlipf | G01L 5/161 |
| 2005/0120809 A1 * | 6/2005 | Ramming | G01L 5/161 73/862.044 |
| 2006/0107761 A1 * | 5/2006 | Meyer | G01L 1/2206 73/862.044 |
| 2006/0130595 A1 * | 6/2006 | Meyer | G01L 5/161 73/862.041 |
| 2006/0213287 A1 * | 9/2006 | Sakano | G01L 5/161 73/862.042 |
| 2013/0239701 A1 | 9/2013 | Huang | |

FOREIGN PATENT DOCUMENTS

| | | |
|---|---|---|
| EP | 1464939 A1 | 10/2004 |
| EP | 1645859 A1 | 4/2006 |
| JP | 60238760 A | 11/1985 |
| JP | H01260759 A | 3/1987 |
| JP | S63231288 A | 9/1988 |
| JP | 2007315878 A | 12/2007 |
| JP | 2010210558 A | 9/2010 |
| WO | WO03006942 A1 | 1/2003 |
| WO | WO2014110682 A1 | 7/2014 |

OTHER PUBLICATIONS

English language abstract for JPS63231288 extracted from espacenet.com database on Oct. 31 2016, 6 pages.
English language abstract for JPH01260759 extracted from espacenet.com database on May 3, 2016, 8 pages.
English language abstract for JP2007315878 extracted from espacenet.com database on May 3, 2016, 34 pages.
English language abstract for JP2010210558 extracted from espacenet.com database on May 3, 2016, 26 pages.
International Search Report for PCT/US2016/016365, dated Jun. 14, 2016; 11 pages.

* cited by examiner

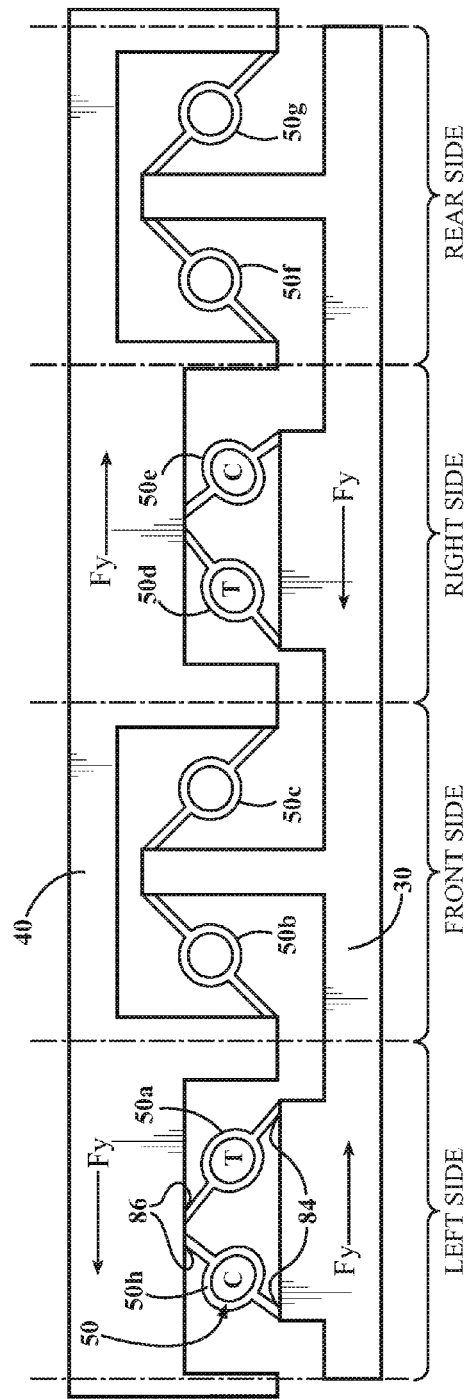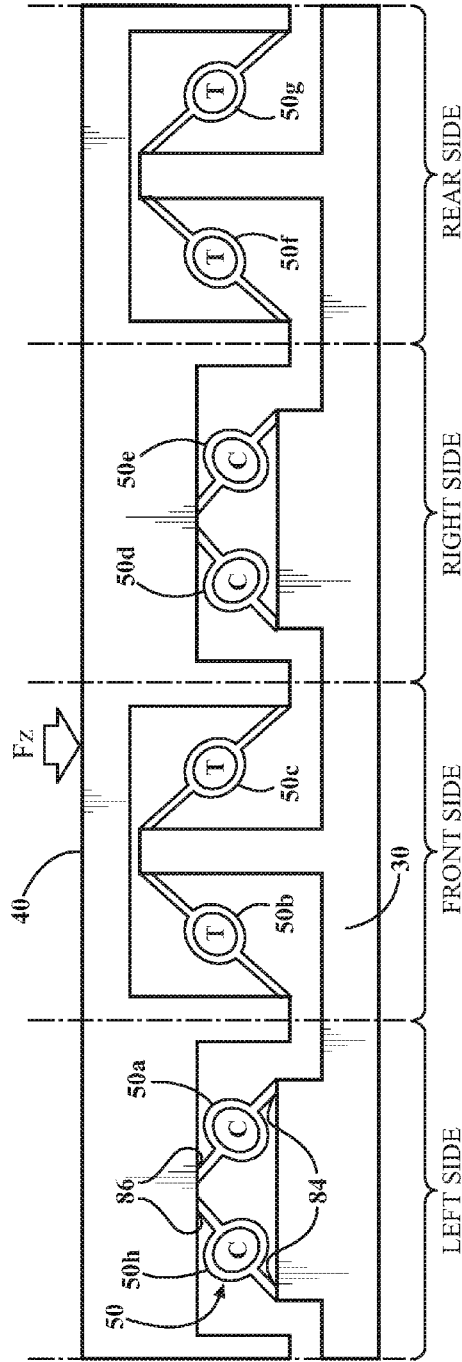

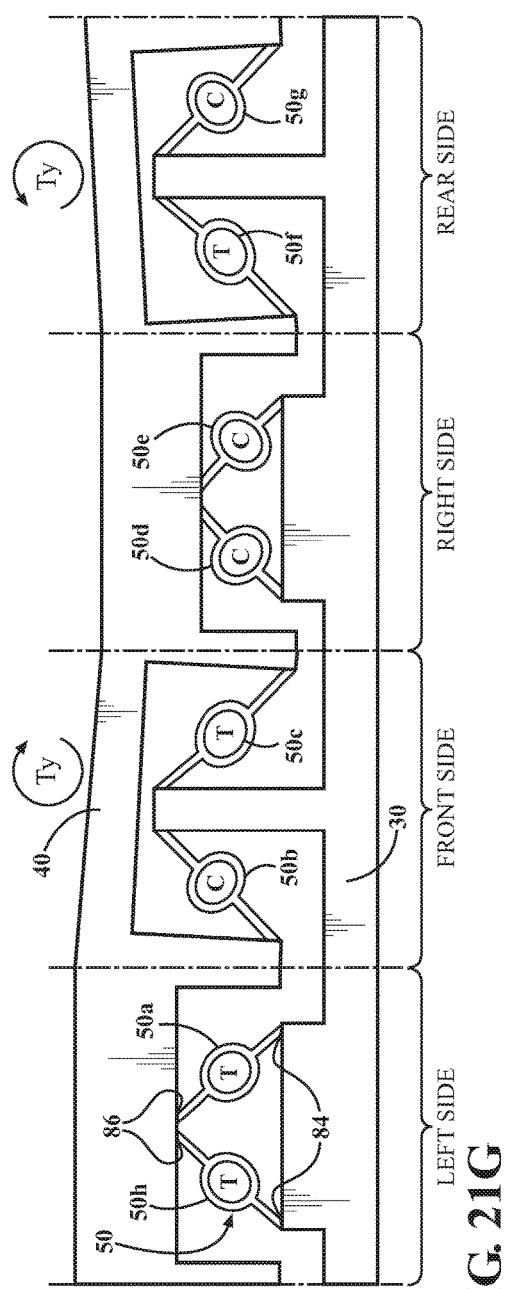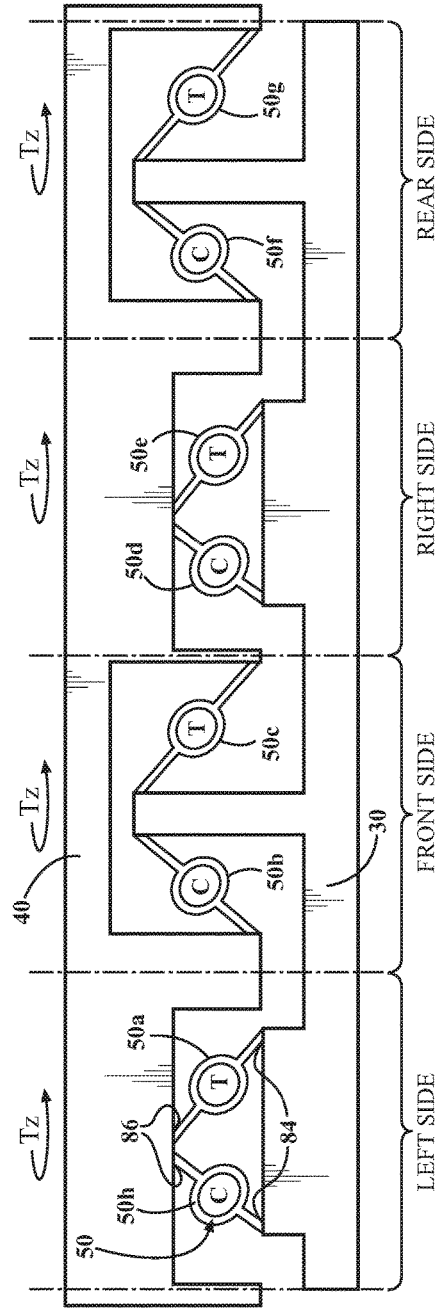
FIG. 21G
FIG. 21H

FORCE/TORQUE TRANSDUCER AND METHOD OF OPERATING THE SAME

CROSS-REFERENCE TO RELATED APPLICATION

The present application claims the benefit of pending U.S. Provisional Patent Application No. 62/111,257, filed Feb. 3, 2015, the entire disclosure of which is hereby incorporated by reference.

TECHNICAL FIELD

The invention relates generally to a force/torque transducer and a method of operating the same.

BACKGROUND

Recently, medical personnel have found it useful to use robotic devices to assist in surgical procedures. A robotic device typically has a moveable arm that comprises one or more moveable links. A controller regulates activation of actuators that position the links. A surgical instrument attaches to a free end of the arm. The surgical instrument interfaces with a surgical site.

Conventionally, a force/torque transducer attaches between the free end of the arm and the surgical instrument. The conventional force/torque transducer cannot measure force or torque directly. Instead, strain on a micro-motion scale is measured and force is deduced based on the measured strain. From these strain measurements, the conventional force/torque transducer deduces forces and torques applied to the instrument. Specifically, as shown in FIG. 1, the force/torque transducer deduces three components of force ($F_x$, $F_y$, $F_z$) and three components of torque ($T_x$, $T_y$, $T_z$). The three components of force ($F_x$, $F_y$, $F_z$) represent axial loads along respective X, Y and Z-axes. The three components of torque ($T_x$, $T_y$, $T_z$) represent rotational loads about the respective X, Y and Z-axes.

The deduced forces and torques may result from various loads. For example, the load may be caused by the instrument pressing against tissue. Alternatively, the medical personnel setting the position and/or orientation of the instrument may apply the load. The conventional force/torque transducer deduces the resulting forces and torques and outputs signals to the controller. The controller processes the signals to determine control signals for determining a target position for the arm. Based on the determination of arm target position, the controller selectively activates the actuators in order to advance the arm to the target position.

A top view of the conventional force/torque transducer is illustrated at 10 in FIG. 2. The conventional force/torque transducer 10 has a fixed member 12 and a moveable member 14. The fixed member 12 is typically mounted to the free end of the arm. The moveable member 14 is secured to the surgical instrument. The moveable member receives the load applied to the surgical instrument. A plurality of spokes 16 connect the fixed and moveable members 12, 14. The spokes 16 bend in response to application of the load to the moveable member 14. The conventional force/torque transducer 10 in FIG. 2 has four spokes 16, however, such conventional transducers may include three spokes 16, and the like.

A plurality of strain gauges 18 attach to each spoke 16 for measuring the strain on the spoke 16. Often, as shown in FIG. 3, the strain gauges 18 attach to the top, bottom, and sides of each spoke 16 for measuring strain on the spokes 16 resulting from X, Y, and/or Z-axis loads.

Each spoke 18 and the strain gauges 18 associated with each spoke 19 collectively form a single-axis load cell in the transducer 10. As such, the conventional, typical force/torque transducer 10 in FIG. 3 comprises four separate load cells.

FIG. 4 illustrates in cross-section the response of the spokes 16 to a load applied axially along the Z-axis. Specifically, as shown in FIG. 4, the load is applied along the Z-axis to the moveable member 14 such that the moveable member 14 moves in a positive Z-axis direction. In response to this load, each of the spokes 16 behaves similarly. That is, each spoke 16 bends in the same direction. Similarly, in response to a load applied in the negative Z-axis direction, each spoke 16 bends in the same direction.

FIG. 5 illustrates from a top view the response of the spokes 16 to a load applied rotationally about the Z-axis. Specifically, as shown in FIG. 5, the load is applied about the Z-axis to the moveable member 14 such that the moveable member 14 rotates counter-clockwise. In response to this load, each of the spokes 16 behaves similarly. That is, each spoke 16 bends in the same direction. Similarly, in response to a load applied in the clockwise direction, each spoke 16 bends in the same direction.

The conventional force/torque transducer 10 is susceptible to providing unreliable measurements because of drift. Generally, drift is an abnormality in the measurements provided by a force/torque transducer.

In the conventional force/torque transducer 10, drift may occur during initialization of the conventional force/torque transducer 10. A strain gauge 18 is a resistor having a value that changes due to strain. As a resistor, the strain gauge 18 consumes power. The consumed power is transformed into heat. The heat of the strain gauge 18 is conducted locally to the material of the spoke 16 upon which the strain gauge 18 rests. An internal stress develops on the spokes 16 because the material of the spokes 16 expands, but is constrained. This stress results in a strain, which, in turn changes the electrical resistance of the strain gauges 18. Consequently, the change in resistance causes a false representation of applied force and/or torque and erroneous force/torque data.

FIG. 6 is a chart of X, Y and Z-axis forces deduced by the conventional force/torque transducer 10 during initial start-up. As observed, the Z-axis force exhibits significant drift, i.e., greater than three pounds, as compared to the X and Y-axis forces. Additionally, unlike the X and Y-axis forces that stabilize, the Z-axis force does not stabilize. Instead, the Z-axis force continuously varies in a range between 2.5 and 3.5 pounds.

FIG. 7 is a chart of X, Y and Z-axis torques deduced by the conventional force/torque transducer 10 during initial start-up. The X and Y-axis torques are stable and exhibit minimal drift. However, the Z-axis torque exhibits significant drift and does not stabilize. Specifically, the Z-axis torque drifts up to 1.4 inch-pounds. Thus, during initial start-up both the Z-axis force and the Z-axis torque suffer from significant drift.

The conventional force/torque transducer 10 is further susceptible to thermal drift. Thermal drift is often caused by thermo-expansion of the strain gauges 18. That is, current flowing through the strain gauges 18 causes the strain gauges 18 to heat up. The increase in the temperature causes the strain gauges 18 to expand locally. The local expansion causes a thermo-strain, which, in turn changes the electrical resistance of the strain gauges 18. Consequently, the change in resistance causes a false representation of applied force and/or torque and erroneous force/torque data.

In one experiment, the conventional force/torque transducer 10 was exposed to heat and the effects of thermal drift on the conventional force/torque transducer 10 were measured. FIG. 8 is a chart of X, Y and Z-axis forces deduced by the conventional force/torque transducer 10 during exposure to heat. The X-axis and Y-axis forces exhibited drift of less than 1 lb. However, the Z-axis force exhibited significant drift of nearly 12 pounds.

As apparent from these results, the conventional force/torque transducer 10 is highly susceptible to drift with respect to Z-axis forces and torques. That is, the conventional force/torque transducer 10 is prone to producing unreliable measurements with respect to Z-axis forces and torques.

The conventional force/torque transducer 10 is most susceptible to drift for Z-axis forces or torques because the spokes 16 exhibit similar bending forces in response to a rotational or axial load applied about/along the Z-axis, as described. Mainly, the negative effects of drift are summed because the bending forces are the same algebraic sign. For example, suppose the total Z-axis force (F) on the conventional force/torque transducer 10 as shown in FIG. 4 is calculated by summing the bending force (F1) on the left-side spoke 16 and the bending force (F2) on the right-side spoke 16. In response to the positive axial Z-axis load, both spokes exhibit positive bending forces. If the bending forces (F1) and (F2) are the same algebraic sign, e.g., positive, then the total Z-axis force is represented by F=|F1+F2|. The total force is the summation of the bending forces, rather than the difference between the bending forces. The same holds true when both bending forces are negative. As such, the conventional force/torque transducer 10 cannot offset bending forces for Z-axis forces or torques. Moreover, the conventional force/torque transducer 10 cannot negate the effects of drift on Z-axis forces or torques. As a result, summation of these similar bending forces causes a substantial amount of systemic mode noise when deducing the Z-axis forces or torques.

Numerous force/torque transducers, besides the conventional force/torque transducer 10 illustrated in FIGS. 2-5, exhibit bending forces of the same algebraic sign in response to applied forces or torques along/about the Z-axis. Such conventional force/torque transducers utilize various types of deforming members other than the spokes 16. For example, a conventional Stewart Platform force/torque transducer, such as the transducer illustrated in JP 2007-315878, equally suffers from the problems described above for the conventional force/torque transducer 10. Mainly, the force/torque transducer in JP 2007-315878 is also unable to adequately eliminate the aforementioned Z-axis drift issues. Specifically, the force/torque transducer in JP 2007-315878 is not capable of self-cancelling the bending forces for applied Z-axis forces. That is, all the deforming members go into tension when a Z-axis force is applied.

Therefore, there remains an opportunity to provide a force/torque transducer that at least solves the aforementioned problems.

SUMMARY

In one embodiment, a force/torque transducer comprises a first member, a second member for receiving a load, and a plurality of load cells connecting the first and second members. The load cells include sensors for measuring physical deformations of the load cells. Sensor measurements are convertible into force/torque measurements using a transformation matrix with M rows and N columns. M is defined by either a number of degrees of freedom monitored by the transducer or a number of load cells employed by the transducer. N is defined by the other one of either the number of degrees of freedom monitored by the transducer or the number of load cells employed by the transducer. Each row or column that corresponds to each one load cell has values relating to the one load cell. Each row or column that corresponds to each one of the degrees of freedom has values relating to the one degree of freedom. A sum of the values in each row or column that corresponds to each degree of freedom is substantially equal to zero.

The transducer provides an arrangement of load cells such that when a systematic noise or offset is applied to all the load cells, the noise or offset is cancelled. This advantage is manifested through the transformation matrix. The load cells exhibit forces of opposite algebraic signs for all loads applied to the second member. Since the forces of the load cells are opposite algebraic signs, the forces cancel or offset one another. As such, the transducer and method effectively eliminate drift, including start-up drift and thermal drift. The transducer and method prevent systematic thermo-expansion or strain from affecting the measured load. The same expansion or strain occurs on all of the individual load cells thereby self-cancelling thermo-strain. The transducer provides differencing in all degrees of freedom. Additionally, the transducer prevents systematic noise from affecting the measured load. In turn, the transducer provides reliable measurements. Additionally, the transducer provides these advantages using a cost-effective and robust configuration.

BRIEF DESCRIPTION OF THE DRAWINGS

Advantages of the present invention will be readily appreciated as the same becomes better understood by reference to the following detailed description when considered in connection with the accompanying drawings wherein:

FIG. 21C is a plan view of the sides of the transducer of FIG. 20 illustrating the load cells transitioning between a rest state and a loaded state in response to an applied Y-axis force.

FIG. 21D is a plan view of the sides of the transducer of FIG. 20 illustrating the load cells transitioning between a rest state and a loaded state in response to an applied downward Z-axis force.

FIG. 21G is a plan view of the sides of the transducer of FIG. 20 illustrating the load cells transitioning between a rest state and a loaded state in response to an applied Y-axis torque.

FIG. 21H is a plan view of the sides of the transducer of FIG. 20 illustrating the load cells transitioning between a rest state and a loaded state in response to an applied Z-axis torque.

DETAILED DESCRIPTION

I. Overview

A force/torque transducer and a method of operating the force/torque transducer are disclosed herein. Referring to the Figures, wherein like numerals indicate like or corresponding parts throughout the several views, the force/torque transducer 20 is generally shown in FIGS. 9-12, 14-17, and 20-31.

Figure 11:
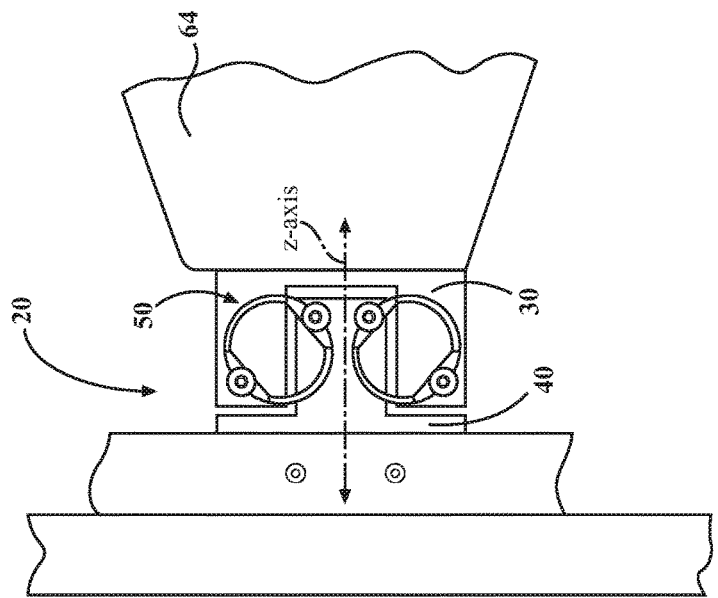
FIG. 11 is an illustration of load cells of the force/torque transducer employed between the instrument and the arm of FIG. 10.

The force/torque transducer 20 has a first member 30 and a second member 40, as shown in one example in FIG. 11. A plurality of load cells 50 connect the first and second members 30, 40. The load cells 50 are single axis or one degree of freedom (1 DOF) load cells. Generally, the first member 30 is fixed. The first member 30 may be fixed to a stationary or moving object. The second member 40 receives a load. The second member 40 moves relative to the first member 30 when the load is applied to the second member 40. The load cells 50 deform upon application of the load to the second member 40. Sensors 54 couple to the load cells 50 for measuring the strain on the load cells 50.

The transducer 20 monitors loads applied to the second member 40 in many degrees of freedom. In one embodiment, the transducer 20 monitors loads applied to the second member 40 in six-degrees of freedom (6 DOF). Loads applied to the second member 40 cause physical strains on the load cells 50 that are measured and transformed into corresponding forces and/or torques. Specifically, the transducer 20 deduces three components of force ($F_x$, $F_y$, $F_z$) and three components of torque ($T_x$, $T_y$, $T_z$). The three components of force ($F_x$, $F_y$, $F_z$) represent axial loads on the second member 40 along respective X, Y and Z-axes. The three components of torque ($T_x$, $T_y$, $T_z$) represent rotational loads on the second member 40 about the respective X, Y and Z-axes. Those skilled in the art appreciate that the transducer 20 may monitor loads applied to the second member 40 in any suitable number of DOFs, including, up to and exceeding 6 DOF.

Figure 1:
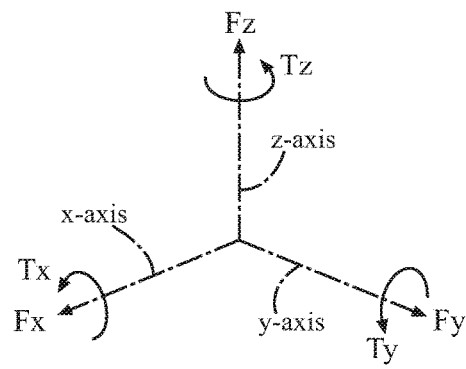
FIG. 1 is a diagram showing the forces and torques deduced by conventional force/torque transducers.
Figure 2:
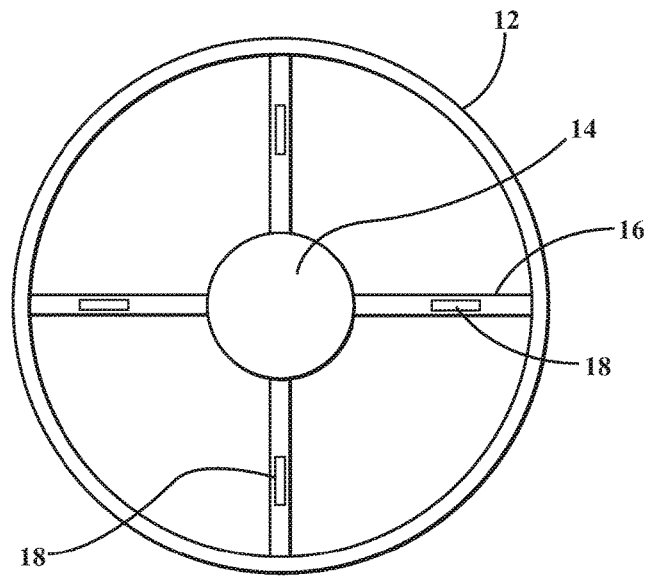
FIG. 2 is a top view of a conventional force/torque transducer.
Figure 3:
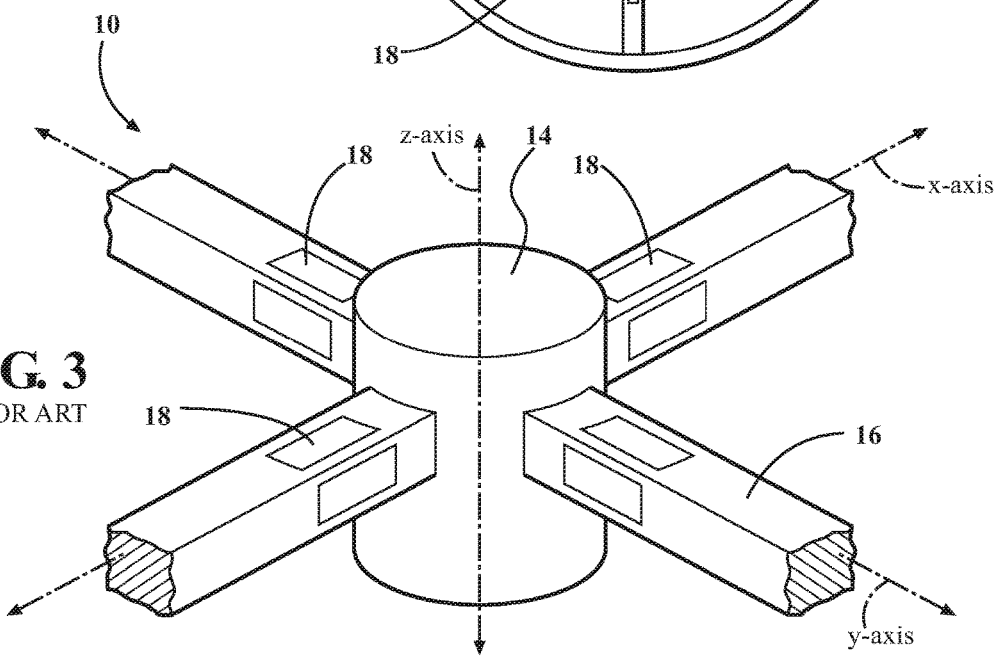
FIG. 3 is an isometric view, partially in cross-section, of the conventional force/torque transducer of FIG. 2.
Figure 4:
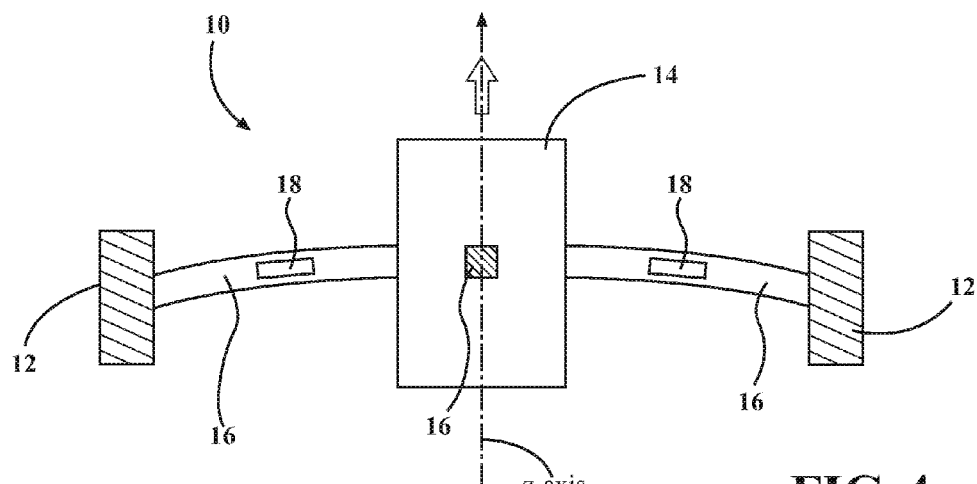
FIG. 4 is a side view, partially in cross-section, of the conventional force/torque transducer of FIG. 2 undergoing a Z-axis force.
Figure 5:
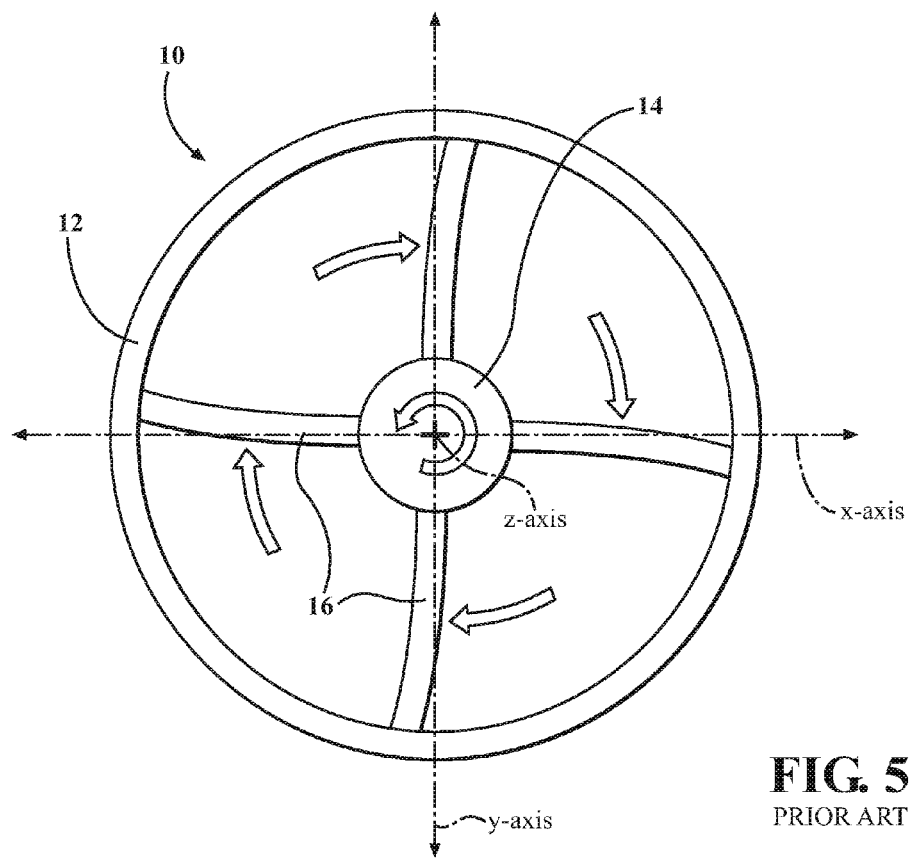
FIG. 5 is a top view of the conventional force/torque transducer of FIG. 2 undergoing a Z-axis torque.
Figure 6:
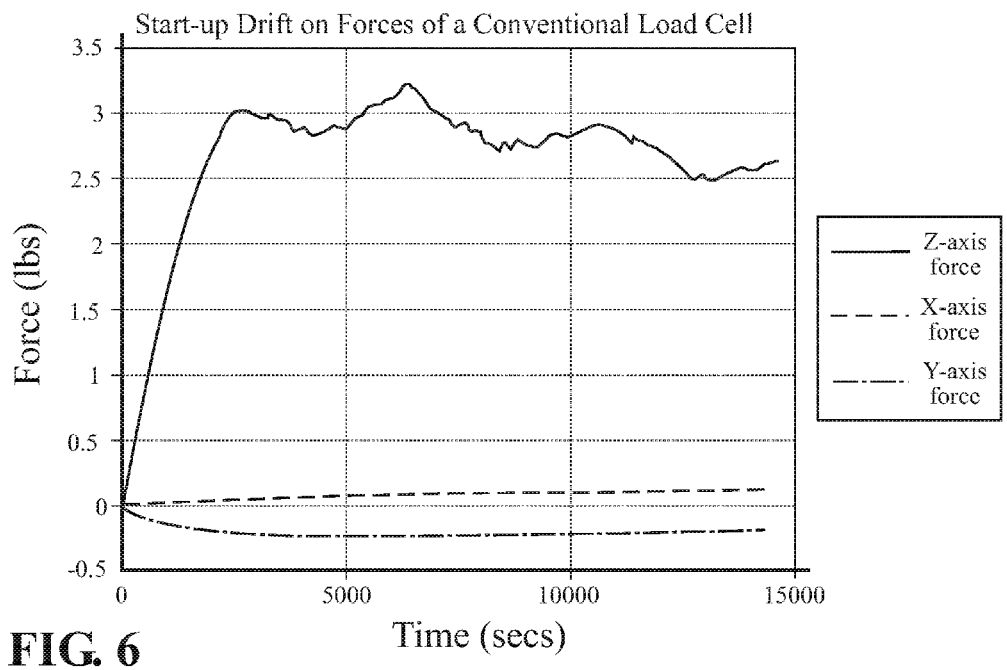
FIG. 6 is a chart of deduced X, Y and Z-axis forces during initial start-up of the conventional force/torque transducer of FIG. 2.
Figure 7:
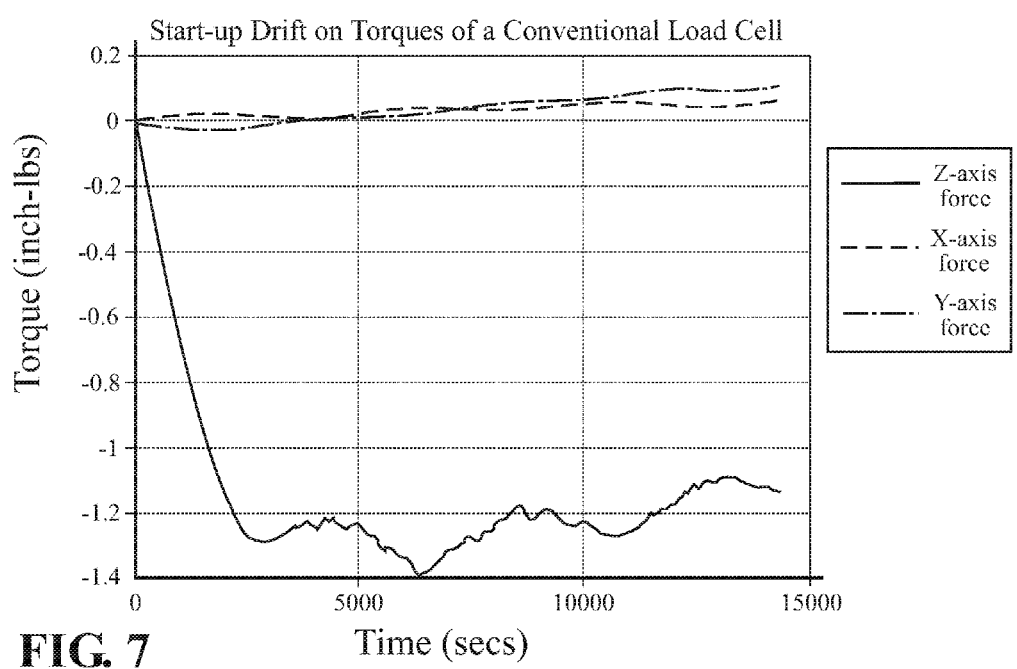
FIG. 7 is a chart of deduced X, Y and Z-axis torques during initial start-up of the conventional force/torque transducer of FIG. 2.
Figure 8:
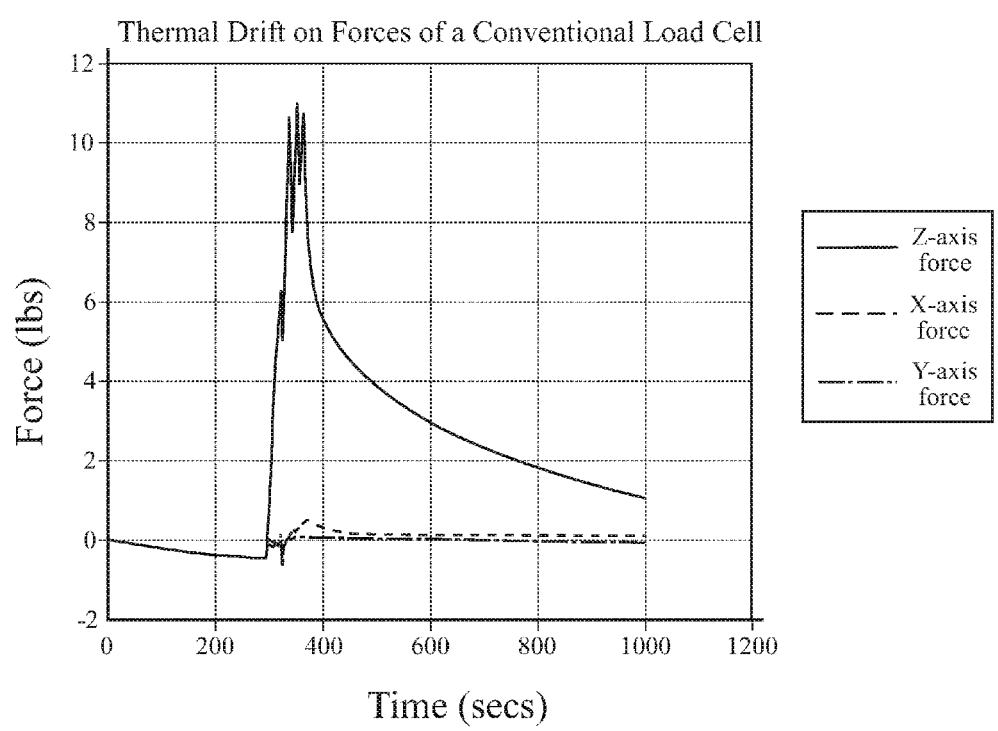
FIG. 8 is a chart of deduced X, Y and Z-axis forces of the conventional force/torque transducer of FIG. 2 during exposure to heat.
Figure 9:
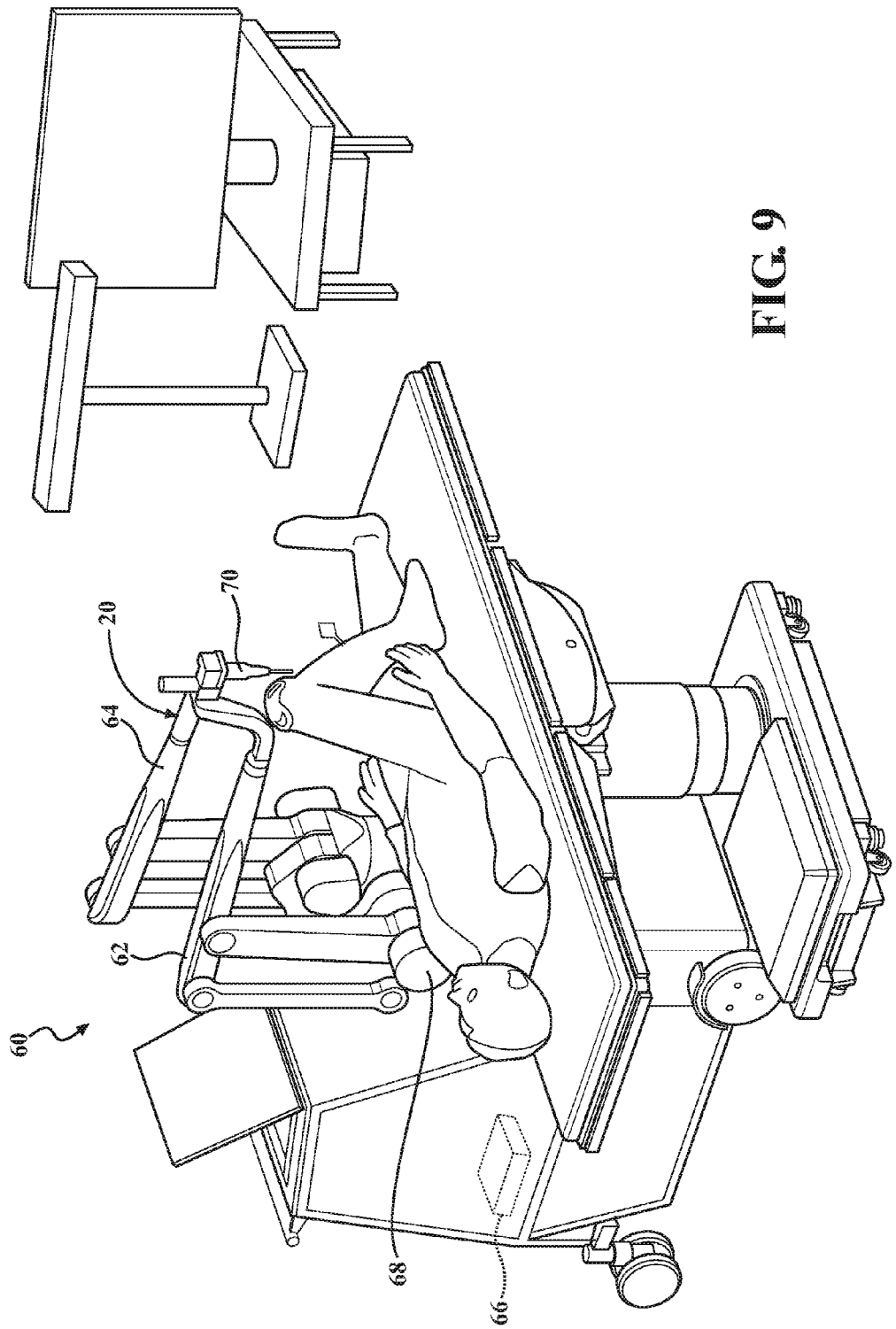
FIG. 9 is a perspective view of a robotic device employing the force/torque transducer according to one embodiment.

The force/torque transducer 20 may be utilized in any system or device in which measuring the stress and strain between two members 30, 40 is desired. One such device is a robotic device 60 for assisting in the performance of surgical procedures, as shown in FIG. 9. The robotic device 60 has a moveable arm 62 that comprises one or more moveable links 64. A controller 66 regulates activation of actuators 68 that position the links 64. An instrument 70, such as a surgical instrument, attaches to a free end of the arm 62. The instrument 70 interfaces with a surgical site.

Figure 10:
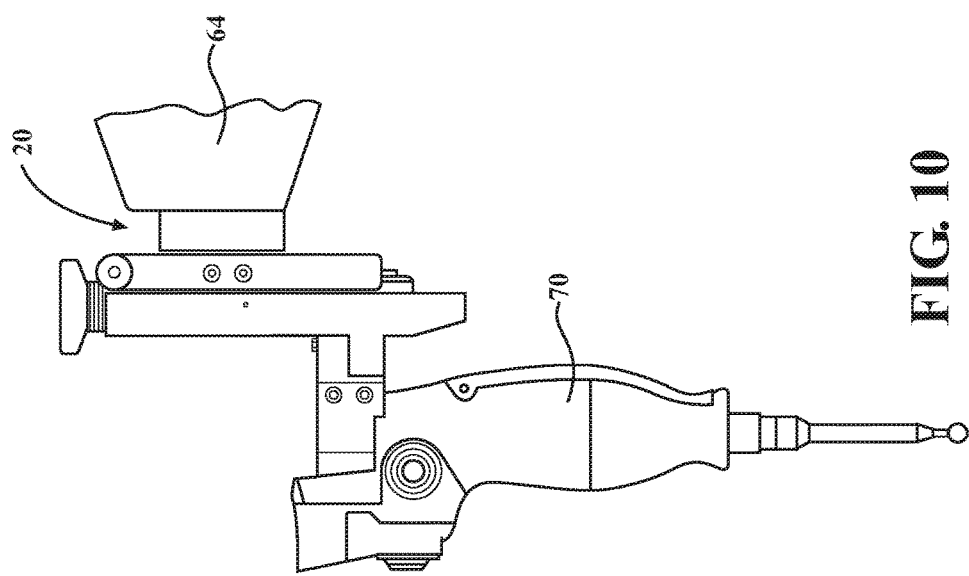
FIG. 10 is a side view of an instrument and an arm of the robotic device of FIG. 9.

In FIG. 9, the force/torque transducer 20 attaches generally between the arm 62 and the instrument 70. More specifically, as shown in FIGS. 10 and 11, the first member 30 of the force/torque transducer 20 is fixed to the free end of the arm 62. The second member 40 of the force/torque transducer 20 attaches to the instrument 70. Of course, the first member 30 may attach to sub-components related to the arm 62, such as a distal end of a coupler of the moveable links 64, and the like. Similarly, the second member 40 may attach to sub-components related to the instrument 70, such as a mounting plate attached to the instrument 70, and the like.

The instrument 70 moves relative to the arm 62 for various reasons. For example, the instrument 70 may press against anatomy of a patient at a surgical site. Alternatively, medical personnel setting the position and/or orientation of the instrument 70 may manually apply a load to the instrument 70. Movement of the instrument 70 causes application of the load on the second member 40. In turn, the transducer 20 deduces the resulting forces and torques applied to the instrument 70 corresponding to the applied load. The transducer 20 outputs signals to the controller 66. The controller 66 processes the signals to determine control signals for determining a target position for the arm 62. Based on the determination of arm target position, the controller 66 selectively activates the actuators 68 in order to advance the arm 62 to the target position.

The force/torque transducer 20 may be utilized in robotic systems having various other configurations in addition to the configuration illustrated and described herein. Additionally, the force/torque transducer 20 may be utilized in systems other than robotic systems. Furthermore, any suitable source may generate the load and the load may be applied for any suitable reason.

II. Force/Torque Transducer

Figure 12:
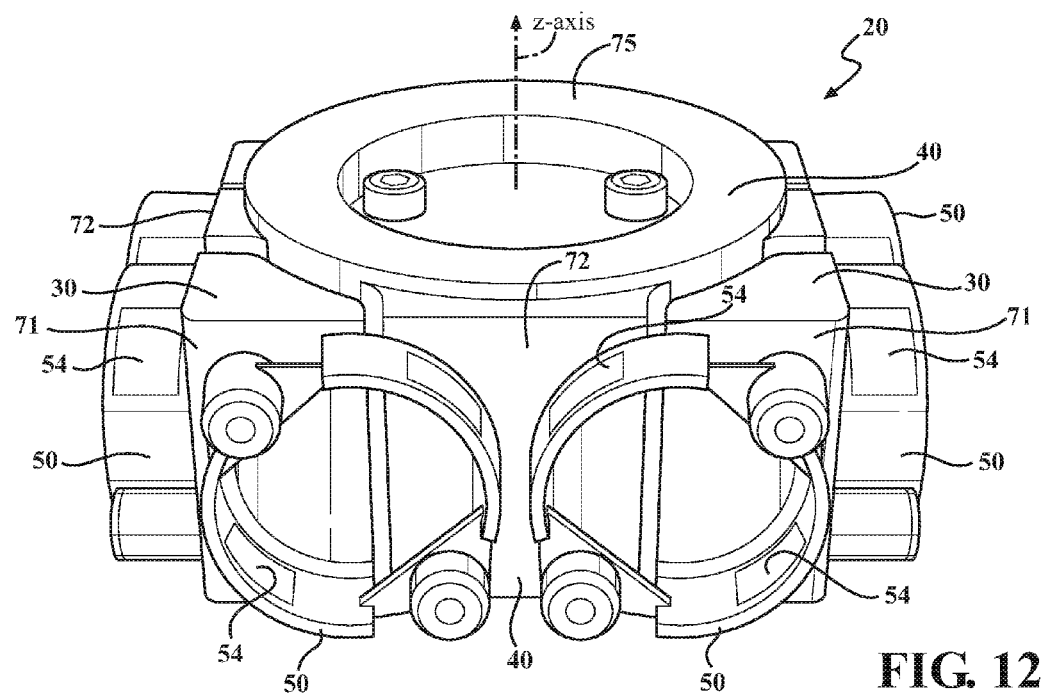
FIG. 12 is a perspective view of one embodiment of the force/torque transducer.

One configuration of the force/torque transducer 20 is illustrated in FIG. 12. The force/torque transducer 20 has a plurality of load cells 50. In FIG. 12, the transducer 20 has eight load cells 50. The load cells 50 physically deform from stress resulting upon application of the load to the second member 40. More specifically, each load cell 50 is configured to go into compression or tension upon application of the load to the second member 40.

Figure 13:
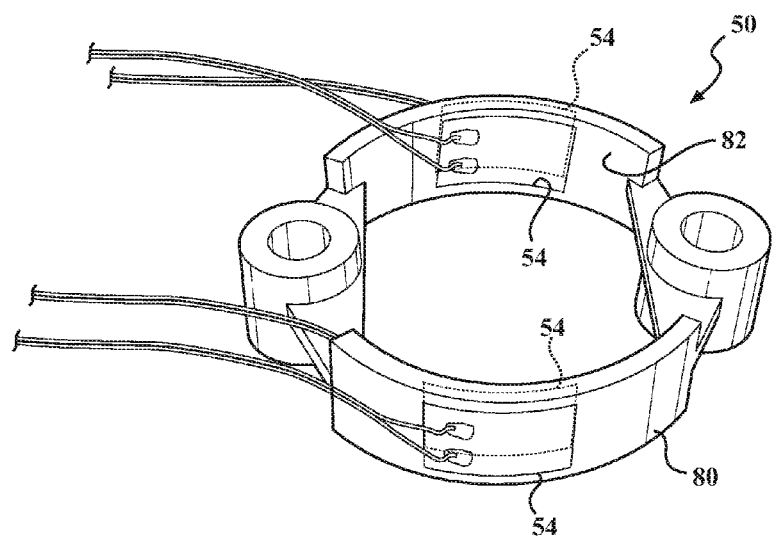
FIG. 13 is a perspective view, partially in phantom, of one embodiment of a load cell of the force/torque transducer of FIG. 12.

Referring to FIG. 13, each load cell 50 of the transducer in FIG. 12 has a hoop configuration. Each load cell 50 has a first surface 80 and an opposing second surface 82. In this embodiment, the first surface 80 is an outer (exterior) surface of the load cell 50 and the second surface 82 is an inner (interior) surface of the load cell 50.

The load cells 50 include sensors 54. The hoop in combination with the sensors 54 attached to the hoop comprises a single element load cell 50. The hoop compresses or tenses in response to the load applied to the second member 40. The sensors 54 are coupled to the load cells 50 for measuring the physical deformations of the hoop. More specifically, the sensors 54 measure strain on the hoop resulting from compression or tension of the surface of the hoop in response to the load applied to the second member 50.

The sensors 54 may have various configurations. In one embodiment, the sensor 54 is a strain gauge. The strain gauge has wires (not shown) of a resistive element that attach to the surface of the load cell 50. A length of the surface of the load cell 50 expands or contracts in response to the load. The strain gauge is a passive device that changes resistance in response to changes in strain on the surface of the load cell 50. That is, a length of the wires changes in response to changes in the length of the surface of the load cell 50. The resistance of the wires changes in response to changes to the length of the electrical wires. Resistance in the strain gauge increases when the surface goes into tension and the resistance in the strain gauge decreases when the surface goes into compression. Strain is proportional to the change in resistance of the strain gauge. The change in resistance is deduced by measuring the voltage across the strain gauge. Any suitable resistance measuring means may measure the change in electrical resistance.

In one embodiment, the strain gauges on the load cell 50 are arranged in sets. For example, the strain gauges may be arranged in a half bridge configuration. Here, the strain gauges are arranged in series circuit configuration such that if the resistance of one strain gauge goes up, the resistance in the other strain gauge(s) goes down. The voltage is measured between the strain gauges. Alternatively, the strain gauges in the load cell 50 are arranged in a full bridge configuration, which comprises two half bridge configurations arranged in a parallel circuit configuration. The full-bridge configuration more sensitively measures small changes in voltage. The sensors 54 may measure deformation according to other suitable embodiments and methods not specifically described herein. Those skilled in the art appreciate that the sensors 54 may have any suitable configuration and position on the load cells 50 and that the configuration and position of the sensors 54 provided on the various load cells 50 depicted throughout the several Figures are not intended to limit the scope of the sensors 54. As such, the configuration and position of the sensors 54 may be other than what is depicted throughout the several Figures.

At least one sensor 54 couples to each load cell 50. In one example, two sensors 54 couple to each load cell 50. For example, one sensor 54 couples to the first surface 80 and another sensor 54 couples to the second surface 82. In another embodiment, as best shown in FIG. 13, four sensors 54 couple to the load cell 50. For example, two sensors 54 couple to the first surface 80 and two sensors couple to the second surface 82.

Any suitable number of sensors 54 may couple to any one, or a number of, surfaces of the load cell 50. Furthermore, the sensors 54 may couple to the load cells 50 according to any suitable method. For example, the sensors 54 may be adhered to the load cells 50 using an adhesive tape, and the like.

The transducer 20 obtains raw gauge values from the sensors 54. A matrix M, such as a transformation or calibration matrix, transforms the raw gauge values into the resulting forces and torques. In other words, the matrix M converts gauge measurements into force and torque measurements. The matrix M may be determined using any suitable method, such as experimental or analytical methods.

Equation (1) illustrates the mathematical relationship between the calibration matrix M, the raw gauge values (e.g., $G_1$ through $G_8$) represented in a gauge matrix on the right side of equation (1), and the resulting forces ($F_x$, $F_y$, $F_z$) and torques ($T_x$, $T_y$, $T_z$), represented in a force matrix on the left side of equation (1):

$$\begin{bmatrix} F_x \\ F_y \\ F_z \\ T_x \\ T_y \\ T_z \end{bmatrix} = [M] \begin{bmatrix} G_1 \\ G_2 \\ G_3 \\ G_4 \\ G_5 \\ G_6 \\ G_7 \\ G_8 \end{bmatrix} \quad (1)$$

In equation (1), the raw gauge values ($G_1$ through $G_8$) are determined by eight different load cells 50. The transformation matrix is configured with M rows and N columns. For equation (1), the number of rows M is defined by the number of degrees of freedom monitored by the transducer 20. Each row corresponds to a different degree of freedom monitored by the transducer 20. No two rows correspond to the same degree of freedom. Since the transducer 20 in FIG. 12 monitors six degrees of freedom ($F_x$, $F_y$, $F_z$, $T_x$, $T_y$, $T_z$), the matrix M has six rows. One row corresponds to force ($F_x$) monitored along the X-axis. One row corresponds to force ($F_y$) monitored along the Y-axis. One row corresponds to force ($F_z$) monitored along the Z-axis. One row corresponds to torque ($T_x$) monitored about the X-axis. One row corresponds to torque ($T_y$) monitored about the Y-axis. One row corresponds to torque ($T_z$) monitored about the Z-axis. The rows may be arranged in any order. Each row that corresponds to each one of the degrees of freedom has values relating to that one degree of freedom. The matrix M has six rows, i.e., one row for each of the force and torque components.

In equation (1), the number of columns N of the matrix is defined by the number of load cells 50 employed by the transducer 20. Since the transducer 20 in FIG. 12 has eight single-axis load cells 50, matrix M has eight columns. Since each load cell 50 produces a raw gauge value, matrix M has the same number of columns as the number of raw gauge values. Thus, in equation (1), the matrix M has eight columns because there are eight raw gauge values. Each column corresponds to a different load cell 50 employed by the transducer 20. No two columns correspond to the same load cell 50. Each column that corresponds to each one load cell 50 has values relating to that one load cell 50. Thus, the matrix M is a 6×8 matrix for the embodiment shown in FIG. 12. The columns may be arranged in any order.

The raw gauge values ($G_1$ through $G_8$) are multiplied by the values of matrix M using matrix multiplication to solve for resulting forces ($F_x$, $F_y$, $F_z$) and torques ($T_x$, $T_y$, $T_z$). The values of the rows and columns in matrix M are described in additional detail below. The matrix M may be various other sizes depending on how many load cells 50 are utilized.

The number of load cells 50 may be greater than or equal to the number of degrees of freedom monitored by the transducer 20. The number of load cells 50 may exceed the number of degrees of freedom monitored by the transducer 20 to facilitate easier manufacture and design of the transducer 20. Generally, however, the number of degrees of freedom cannot be greater than the number of load cells 50.

In some instances, the matrix M may be transposed such that the rows M are defined by the number of load cells 50 employed by the transducer 20 and the columns N are defined by the number of degrees of freedom monitored by the transducer 20. In such instances, the force matrix and gauge matrix are also transposed and are represented by row vectors, rather than column vectors. Those skilled in the art appreciate that the matrix M may be transposed for other reasons not described herein. Additionally, the matrix may be various other sizes depending on the degrees of freedom monitored and the load cells 50 employed by the transducer 20.

In FIGS. 14-17, each load cell 50 connects to the first member 30 at a first interface 84 and to the second member 40 at a second interface 86. Each load cell 50 has a length. In FIGS. 14-17, the length of the load cell 50 is measured in a straight line between the first and second interfaces 84, 86 such that the straight line bisects a circumference of the hoop. Although, as described below, the length of the load cell 50 may be measured other ways depending on the configuration of the first and second interfaces 84, 86.

Figure 14:
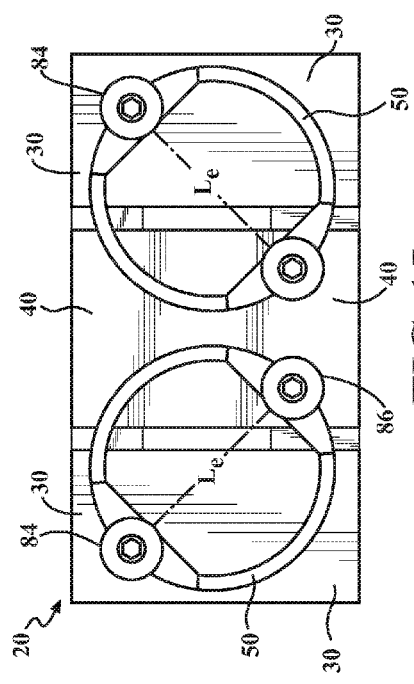
FIG. 14 is a right side view of the force/torque transducer of FIG. 12 at rest.
Figure 15:
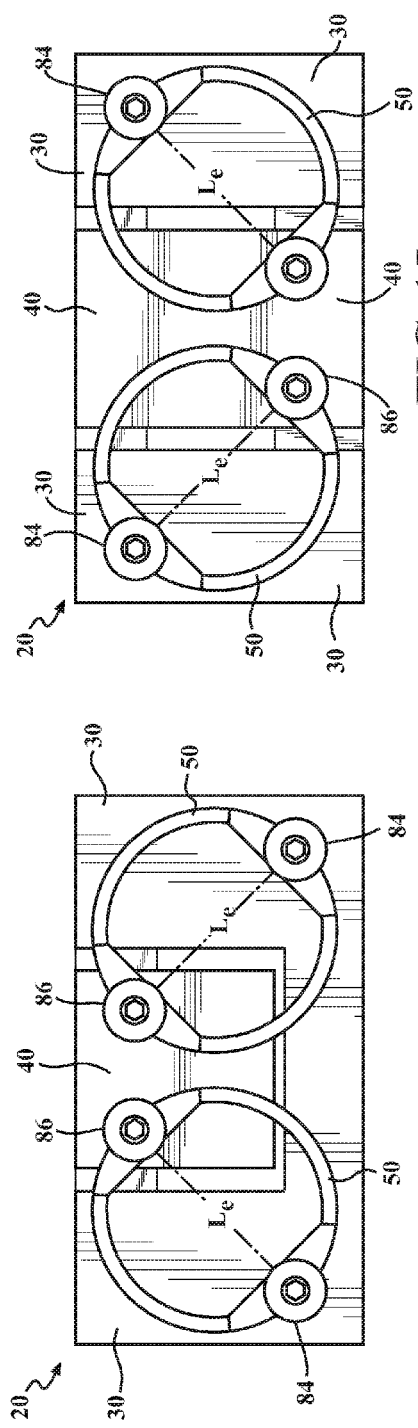
FIG. 15 is a front side view of the force/torque transducer of FIG. 12 at rest.

FIGS. 14 and 15 illustrate respective right side and front side views of the force/torque transducer 20 of FIG. 12. In FIGS. 14 and 15, a Z-axis load is not yet applied to the force/torque transducer 20. As such, the load cells 50 are neither going into compression nor tension. That is, the load cells 50 are at rest and exhibit an equilibrium length, i.e., $L_e$.

Figure 16:
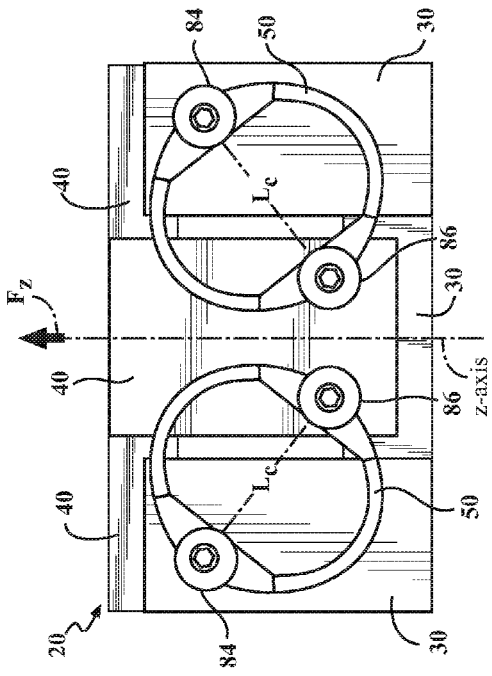
FIG. 16 is a right side view of the force/torque transducer of FIG. 12 undergoing a Z-axis force.
Figure 17:
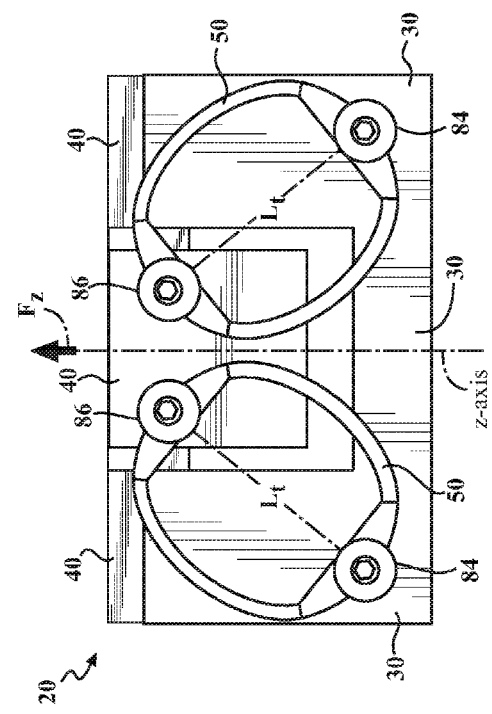
FIG. 17 is a front side view of the force/torque transducer of FIG. 12 undergoing the Z-axis force.

FIGS. 16 and 17 illustrate the respective right side and front side views of the force/torque transducer 20 after a Z-axis load is applied. Here, the second member 40 moves relative to the first member 30 with respect to the Z-axis. More specifically, the first and second members 30 separate along the Z-axis. Such separation occurs on both the front and right sides of the force/torque transducer 20. As a result, the load cells 50 deform from the equilibrium length $L_e$. Motion of the second member 50 and deformation of the load cells 50 may be micro-motion and not readily discernible by the human eye. Thus, the motion of the second member 50 and deformation of the load cells 50 in FIGS. 16 and 17 is exaggerated for simplicity in illustration.

Despite such separation, the load cells 50 on the right side (FIG. 16) go into tension, while on the load cells 50 on the front side (FIG. 17) go into compression. Specifically, the load cells 50 on the right side (FIG. 16) stretch to a tensile length $L_t$ that is longer than the equilibrium length $L_e$. On the other hand, the load cells 50 on the front side (FIG. 17) compress to a compression length $L_c$ that is shorter than the equilibrium length $L_e$. Although only the front and right sides of the force/torque transducer 20 are illustrated in FIGS. 14-17 for simplicity, the remaining other sides, i.e., the back side and left side, exhibit similar behavior to the front and right side, respectively.

A theoretical matrix M was generated for one embodiment, i.e., the force/torque transducer 20 of FIG. 12. The matrix is derived from the geometry layout of the transducer 20, and the geometrical relationship between the members 30, 40 and the load cells 50.

Figure 21A:
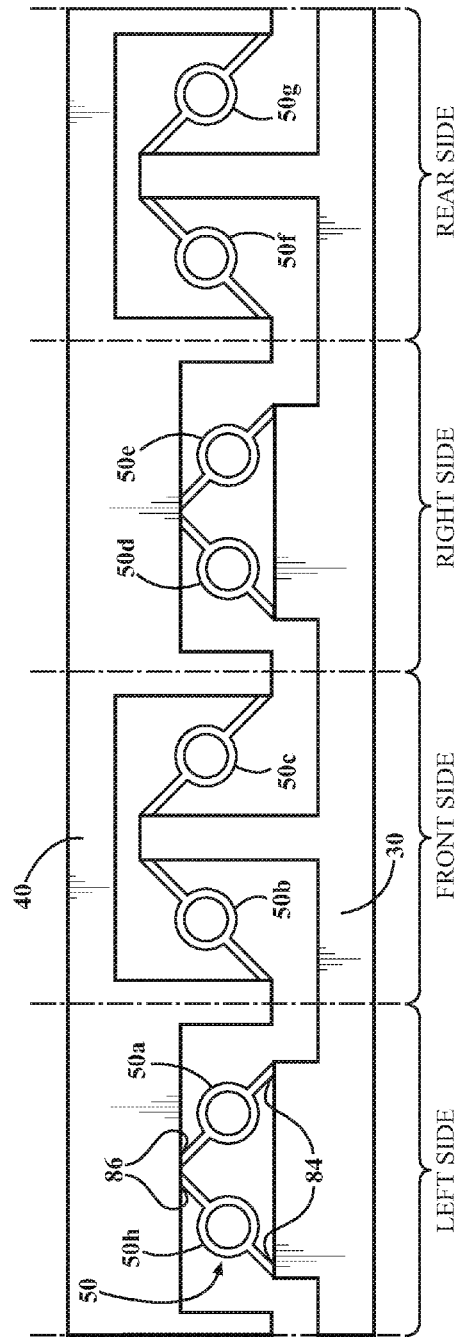
FIG. 21A is a plan view of the sides of the transducer of FIG. 20 illustrating the load cells in an at rest state.

The eight load cells 50a-50h of the transducer 20 are laid out flat in plan views in FIG. 21A for simplicity in illustration. The transducer 20 has eight load cells 50 such that the matrix M has eight columns. In the matrix M, the first column from the left includes calibration values for the load cell 50a on the left side, which is nearest to the front side. The second and third columns from the left include calibration values for the two load cells 50b, 50c on the front side. The fourth and fifth columns from the left include calibration values for the two load cells 50d, 50e on the right side. The sixth and seventh columns from the left include calibration values for the two load cells 50f, 50g on the rear side. The eighth column from the left includes calibration values for the remaining load cell 50h on the left side, which is nearest to the rear side.

As described above, the six rows of the matrix M correspond to the six degrees of freedom monitored by the transducer 20. Mainly, from top to bottom, the rows of the matrix M are assigned to the three forces ($F_x$, $F_y$, $F_z$) and three torques ($T_x$, $T_y$, $T_z$), respectively. The matrix M determined for this embodiment is as follows:

$$[M] = \begin{bmatrix} 0 & -0.7 & 0.7 & 0 & 0 & 0.7 & -0.7 & 0 \\ -0.7 & 0 & 0 & -0.7 & 0.7 & 0 & 0 & 0.7 \\ 0.7 & -0.7 & -0.7 & 0.7 & 0.7 & -0.7 & -0.7 & 0.7 \\ 0.56 & -0.78 & -0.78 & 0.56 & -0.56 & 0.78 & 0.78 & -0.56 \\ -0.79 & 0.07 & -0.07 & 0.78 & 0.79 & -0.07 & 0.07 & -0.78 \\ -0.78 & 0.78 & -0.78 & 0.78 & -0.78 & 0.78 & -0.78 & 0.78 \end{bmatrix}$$

Assuming, for simplicity, that the eight raw gauge values ($G_1$ through $G_8$) each have a value of one, the result of the matrix multiplication from equation (1) is substantially zero for each of the forces ($F_x$, $F_y$, $F_z$) and torques ($T_x$, $T_y$, $T_z$). The sum of the values in each row that corresponds to each degree of freedom is substantially equal to zero.

For example, if one were to add each of the values in the top row of matrix M, which corresponds to degree of freedom $F_x$, the sum of those values would be equal to zero, as shown below:

$$[0+-0.7+0.7+0+0+0.7+-0.7+0]=0$$

The same is true for all other rows corresponding to the remaining degrees of freedom. The closer the sum is to zero, the greater effects of self-cancelling. Thus, the force/torque transducer 20 is not susceptible to any systematic drift for any of the forces ($F_x$, $F_y$, $F_z$) and torques ($T_x$, $T_y$, $T_z$).

Those skilled in the art recognize that the sum need not be exactly zero. The sum may result in a negligible non-zero number, including, for example, a decimal value. In one example, substantially equal to zero means that the absolute value of the sum is equal to or less than one percent of the absolute value of the greatest value in the row. For example, consider the following row:

$$(F_x)=[0, 26000, 0, -13100, 0, -13100]$$

In this example, the sum of the values of the row is not exactly equal to zero. Specifically, the sum of the values is equal to −200 and the absolute value of the sum is equal to 200. However, the absolute value of the sum is substantially equal to zero when taken in context of the absolute value of the greatest value, i.e., 26000. Mainly, the absolute value of the sum, i.e., 200 is 0.76% of 26000. In other words, 200 is less than one percent of the absolute value of 26000.

Several observations are made with respect to matrix M above. For example, values in the matrix that are zero suggest that the respective load cell 50 associated with the column having the zero value does not undergo strain in response to load applied for the degree of freedom associated with the row having the zero value. The load cell 50 associated with the column having the zero value may undergo other forces, such as a sheer force. However, the load cell 50 does not generally go into compression or tension in response to the load applied for the respective degree of freedom.

Values in the matrix that are non-zero suggest that the respective load cell 50 associated with the column having the non-zero value undergoes some strain in response to load applied for the degree of freedom associated with the row having the non-zero value. The magnitude of the non-zero value may or may not be proportional to the amount of strain that the load cell 50 undergoes in response to the load.

Values of the matrix that are negative suggest that the load cell 50 associated with the column having the negative value undergoes tension in response to load applied for the degree of freedom associated with the row the negative value.

Values of the matrix that are positive suggest that the load cell 50 associated with the column having the positive value is undergoing compression in response to load applied for the degree of freedom associated with the row the positive value.

If the applied force is inverted, the effects of the positive and negative values in the matrix M are inverted. In such instances, the same negative value of the matrix can suggest that the load cell 50 undergoes compression, rather than tension, in response to the inverted force. Similarly, the same positive value suggests that the load cell 50 undergoes tension, rather than compression, in response the inverted load.

The matrix M may have various features and embodiments. In some instances, for example, half of the values are zero in at least one of the rows corresponding to one of the degrees of freedom. For example, in matrix M above, half of the values are zero in the first and second rows ($F_x$), ($F_y$). This suggests that half of the load cells 50 do not undergo strain in response to axial loads applied along the X or Y axes.

Additionally, the sum of a first half of the values in at least one of the rows may be substantially equal to zero and the sum of a remaining second half of the values in that row may be substantially equal to zero. In other words, the sum of the left-most four values in at least one of the rows is substantially equal to zero and the sum of the right-most four values in at least one of the rows is substantially equal to zero. In some instances, the sum of a first half of the values for every row is substantially equal to zero and the sum of a remaining second half of the values for every row is substantially equal to zero.

Furthermore, half of the values may be negative in at least one of the rows corresponding to one of the degrees of freedom. Specifically, in matrix M above, half of the values are negative in the lower four rows ($F_z$), ($T_x$), ($T_y$), ($T_z$). This suggests that half of the load cells 50 undergo tension in response to a load applied for the degree of freedom associated with the row having the negative values.

Additionally, half of the values may have the same absolute value in at least one of the rows corresponding to one of the degrees of freedom. For example, in rows ($F_x$), ($F_y$), ($F_z$), half of the values have an absolute value of 0.7, and in row ($T_x$) half of the values have an absolute value of 0.78. This suggests that, for the degree of freedom associated with the row having half of the values with the same absolute value, half of the load cells 50 undergo strain of the same magnitude in response to load applied.

In some instances, all of the values have the same absolute value in at least one of the rows corresponding to one of the degrees of freedom. For example, in matrix M above, the values for the third row ($F_z$) all have the same absolute value, e.g., 0.7. Similarly, the values for the sixth row ($T_z$) all have the same absolute value, e.g., 0.78. This suggests that, for the degree of freedom associated with the row having all of the values with the same absolute value, every load cell 50 undergoes strain of the same magnitude in response to load applied.

All of the values may be non-zero in at least one of the rows corresponding to one of the degrees of freedom. For example, in matrix M, all of the values for each of the rows ($T_x$, $T_y$, $T_z$) are non-zero. In other words, no value is zero is any of these rows. This suggests that, for the degree of freedom associated with row having all non-zero values, each load cell 50 undergoes some strain in response to load applied.

In other instances, at least two values may be non-zero and identical in each row corresponding to one of the degrees of freedom. For example, in each of rows ($F_x$), ($F_y$), ($F_z$), ($T_y$) at least two values are 0.7, in row ($T_x$) at least two values are 0.56, and in row ($T_z$) at least two values are 0.78. This suggests that, for each degree of freedom, at least two load cells 50 behave identically in response to load applied.

Moreover, every other value in at least one of the rows corresponding to one of the degrees of freedom may have opposite algebraic signs. For example, in matrix M above, every other value in the sixth row ($T_z$) is of opposite algebraic sign. This suggests that half the load cells 50 go into compression and half go into tension in response to Z-axis torques. This also suggests that adjacent load cells 50 behave oppositely in response to Z-axis torques.

Since the sum of the values in each row that corresponds to each degree of freedom is substantially equal to zero, the values cancel each other out. Cancelling of the values may be done according to various methods. In one example, each one of the non-zero values is canceled out by another one of the non-zero values in the row. For example, in row ($F_x$), each value of 0.7 is cancelled out by one value of −0.7. In another example, one of the non-zero values is canceled out by a combination of at least two other non-zero values in the row. An example of this situation is illustrated in the matrix row below:

$(F_x)=[0, 26000, 0, -13000, 0, -13000]$

In this row, for example, $(F_x)$, the value 26000 is cancelled out by a combination of −13000 and −13000. In other words, one value is cancelled out by the combination of two other values. Thus, in this situation, the cancellation is not one-to-one. In this example, the absolute value of one of the values is twice the absolute value of another one of the values. In other words, the absolute value of 26000 is twice the absolute value of −13000. One value may be cancelled by more than two other values in the same row.

Each of the observations realized above for the matrix may apply equally and fully to instances wherein the matrix is inverted such that each column corresponds to each degree of freedom. The matrix M may realize any single one or combination of these observations relating to the values of the matrix. These advantages are obtainable for the other embodiments described herein. Thus, the calibration values in the matrix M may be different depending on the given embodiment.

Figure 18:
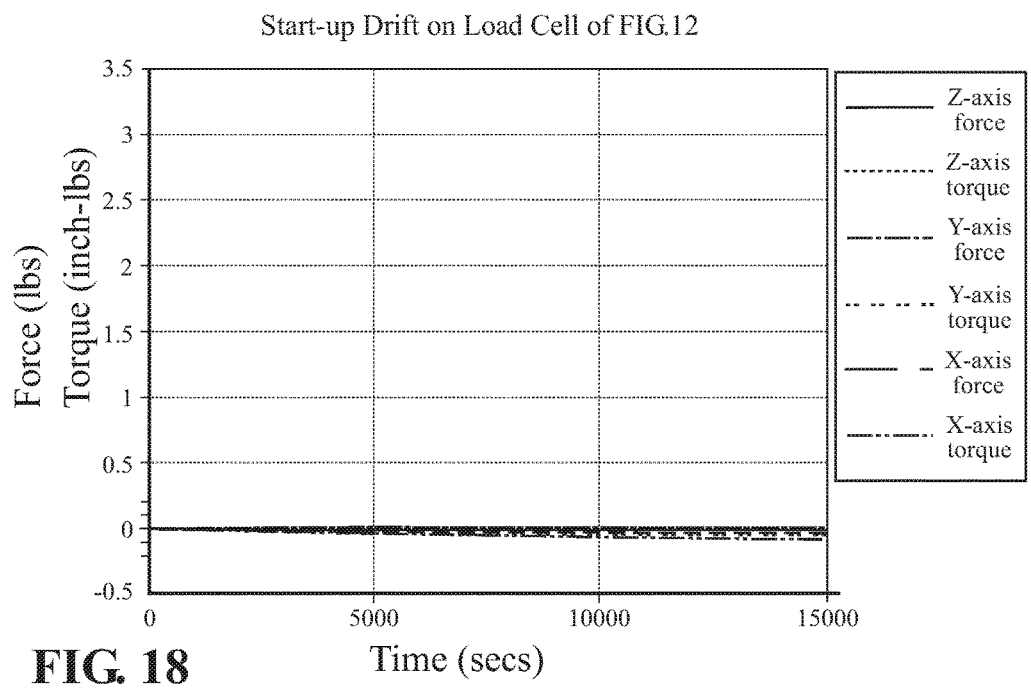
FIG. 18 is a chart of deduced X, Y and Z-axis forces and torques during initial start-up of the transducer of FIG. 12.

In one experiment, the force/torque transducer 20 of FIG. 12 was tested during start-up over a predetermined period. FIG. 18 is a chart of deduced X, Y and Z-axis forces and torques of the force/torque transducer 20 during initial start-up. Advantageously, in FIG. 18, the Z-axis force and torque are stable and do not vary. The Z-axis force and torque exhibits minimal drift, i.e., less than 0.02 pounds (inch-pounds) over the period. These results were achieved with the theoretical matrix M values provided above.

The load cells 50 of the transducer 20 are not constrained between two rigid and fixed (non-moving) parts. When individual load cells are combined into a multi-degree of freedom load cell, the individual load cells are usually constrained. Here, each load cell 50 stands alone and is not combined into a multi-axis or multi-load cell system. Since the load cells 50 are not constrained, the sensors 54 expand by the same amount. By expanding by the same amount, the sensors 54 have a self-cancelling effect. Mainly, each of the individual load cells heats up due to resistive heating. However, the geometry of the transducer 20, as described herein, causes equal and opposite thermo-strain. This opposing net effect is subtracted, thereby cancelling systematic errors. Thus, power dissipated to the material of the load cells 50 during initialization is offset.

Figure 19:
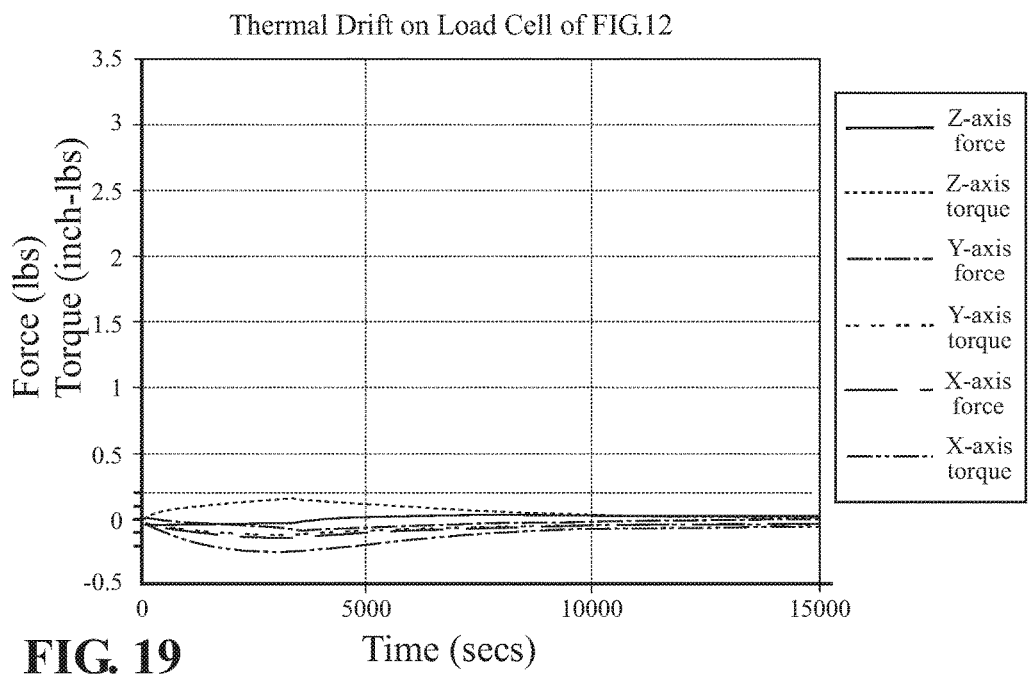
FIG. 19 is a chart of deduced X, Y and Z-axis forces and torques of the transducer of FIG. 12 during exposure to heat.

In another experiment, the force/torque transducer 20 of FIG. 12 was exposed to heat and the effects of thermal drift on the force/torque transducer 20 were measured. FIG. 19 is a chart of X, Y and Z-axis forces and torques deduced by the force/torque transducer 20 during exposure to heat. The force/torque transducer 20 was exposed to 100 degrees Fahrenheit for a predetermined period. The X, Y and Z-axis forces and torques drift by less than 0.1 lb, nearly one-tenth of the drift exhibited by the conventional force/torque transducer 10. More significantly, the Z-axis force and torque exhibited minimal drift. The deduced Z-axis drift for the conventional force/torque transducer 10 is nearly 120 times greater than the deduced the Z-axis drift for the force/torque transducer 20 of FIG. 12. These results were achieved with the theoretical matrix M values provided above.

As evidenced by these results, the force/torque transducer 20 and method significantly eliminate start-up and thermal drift, as well as systematic noise interfering with measurement of loads applied to the second member 40. In turn, the force/torque transducer 20 provides reliable measurements. Additionally, the force/torque transducer 20 provides these advantages using a cost-effective and robust configuration.

III. Loading

Figure 20:
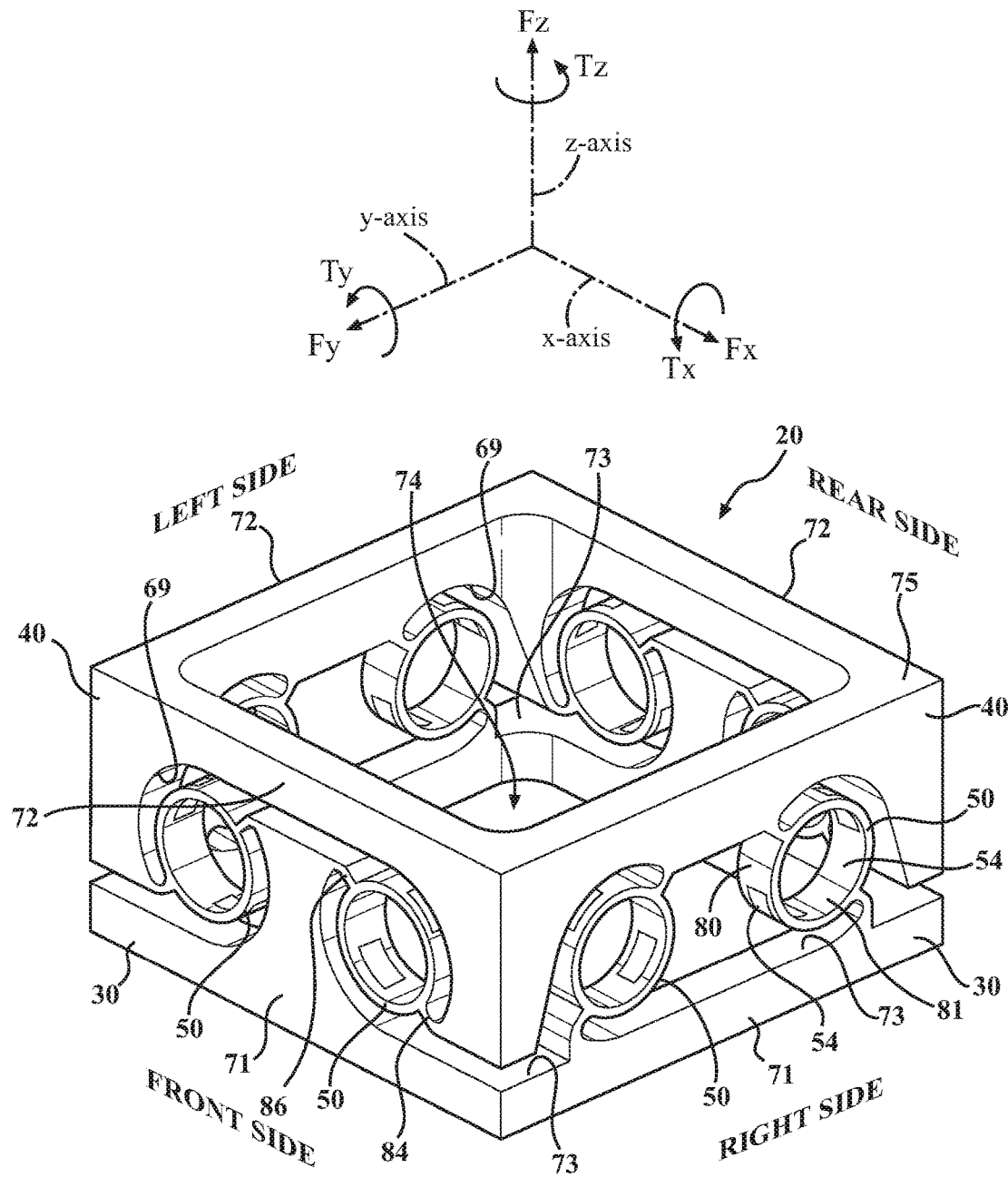
FIG. 20 is a perspective view of another embodiment of the force/torque transducer.

Another example of the force/torque transducer 20 is illustrated in FIG. 20. The force/torque transducer 20 shown in FIG. 20 is configured such that one of the load cells 50 is configured to go into compression and another one of the load cells 50 is configured to go into tension for all loads applied to the second member 40. Here, there is no motion of the second member 40 that causes all of the load cells 50 to go into compression or that causes all of the load cells 50 to go into tension. In other words, there is least one load cell 50 that goes into compression and at least one load cell that goes into tension for all loads applied to the second member 40.

FIGS. 21A-21H schematically illustrate each of sides of the force/torque transducer 20 of FIG. 20 in an rolled-out, plan view, to illustrate how the load cells 50a-50h react in various loading situations. FIGS. 21A-21H illustrate the load cells 50a-50h in various loaded states, thereby illustrating a transition between the rest state and the loaded states.

FIG. 21A illustrates the load cells 50a-50h in a rest state. In other words, the load cells 50a-50h are not undergoing any tension or compression. There is no load yet applied to the second member 40.

Figure 21B:
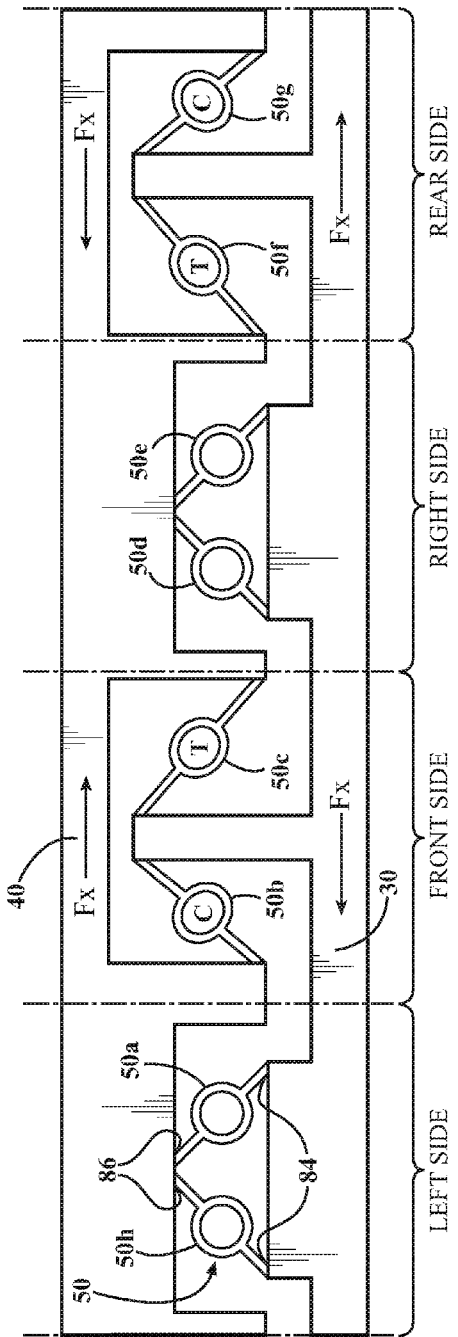
FIG. 21B is a plan view of the sides of the transducer of FIG. 20 illustrating the load cells transitioning between a rest state and a loaded state in response to an applied X-axis force.

In FIG. 21B, an X-axis force is applied to the second member 40. Specifically, the X-axis force is applied in a direction from the left side to the right side of the transducer 20, as shown in FIG. 20. As a result, half of the load cells 50a-50h experience strain and half of the load cells 50a-50h experience no strain. Specifically, load cells 50b and 50g go into compression, designated by C, and load cells 50c and 50f go into tension, designated by T. This is consistent with the matrix M showing half of the values being zero and half the values being non-zero in the row corresponding to $F_x$. More specifically, have the non-zero values are negative and half are positive, which is consistent with load cells 50b and 50g going into compression and load cells 50c and 50f going into tension.

In FIG. 21C, a Y-axis force is applied to the second member 40. Specifically, the Y-axis force is applied in a direction from the front side to the rear side of the transducer 20. As a result, half of the load cells 50a-50h experience strain and half of the load cells 50a-50h experience no strain. Specifically, load cells 50e and 50h go into compression, designated by C, and load cells 50a and 50d go into tension, designated by T. This is consistent with the matrix M showing half of the values being zero and half the values being non-zero in the row corresponding to $F_y$. More specifically, have the non-zero values are negative and half are positive, which is consistent with load cells 50e and 50h going into compression and load cells 50a and 50d going into tension.

In FIG. 21D, a Z-axis compressive force is applied to the second member 40. Specifically, the Z-axis force is applied to the second member 40 in a downward (negative) direction. As a result, half of the load cells 50 go into compression and half go into tension. Specifically, load cells 50a, 50d, 50e, 50h go into compression and load cells 50b, 50c, 50f, 50g go into tension. This is consistent with the matrix M showing all values being non-zero with half values being positive and half being negative in the row corresponding to $F_z$.

Figure 21E:
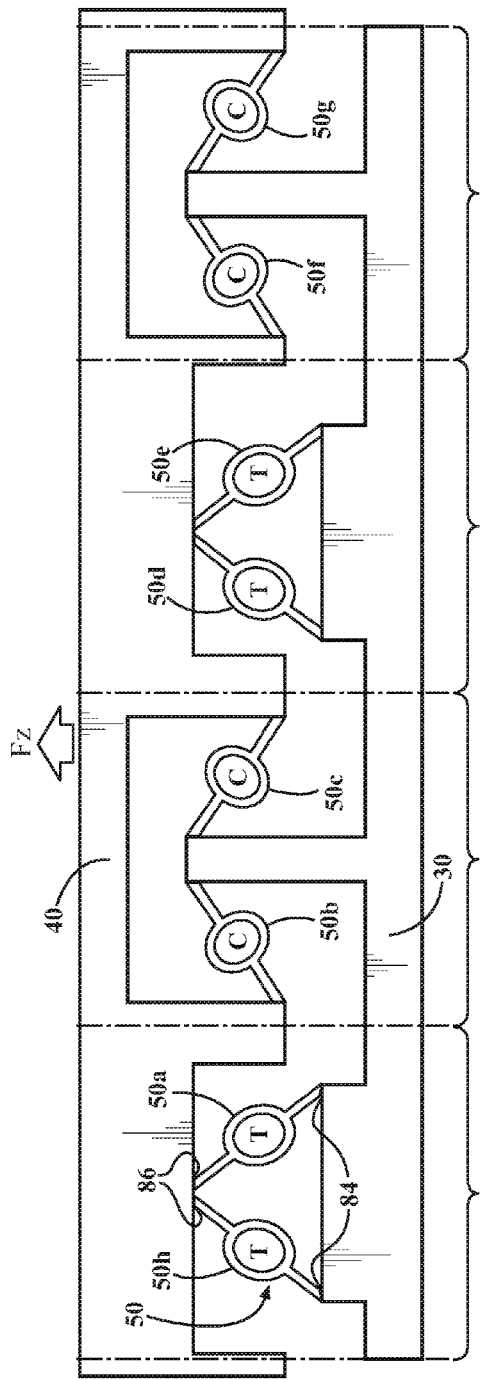
FIG. 21E is a plan view of the sides of the transducer of FIG. 20 illustrating the load cells transitioning between a rest state and a loaded state in response to an applied upward Z-axis force.

In FIG. 21E, a Z-axis tensile force is applied to the second member 40. Specifically, the Z-axis force is applied to the second member 40 in an upward (positive) direction. Here, the result is opposite of that in FIG. 21D. Mainly, load cells 50a, 50d, 50e, 50h go into tension and load cells 50b, 50c, 50f, 50g go into compression. This is consistent with the matrix M showing all values being non-zero with half values being positive and half being negative in the row corresponding to $F_z$. Here, since the Z-axis force is inverted (negative), the effects of the positive and negative values in the matrix M are inverted. Specifically, a negative value in row $F_z$ suggests that the load cell 50 undergoes compression and a positive value suggests that the load cell 50 undergoes tension.

Different load cells 50 may go into compression or tension depending on the load applied to the second member 40. For example, referring to FIG. 21E, load cell 50b goes into compression and load cell 50a goes into tension for the given Z-axis load applied to the second member 40. Meanwhile, load cell 50b may go into compression and load cell 50a may go into tension for another given Z-axis load applied to the second member 40, such as a Z-axis load in the opposite direction, as shown in FIG. 21D.

Figure 21F:
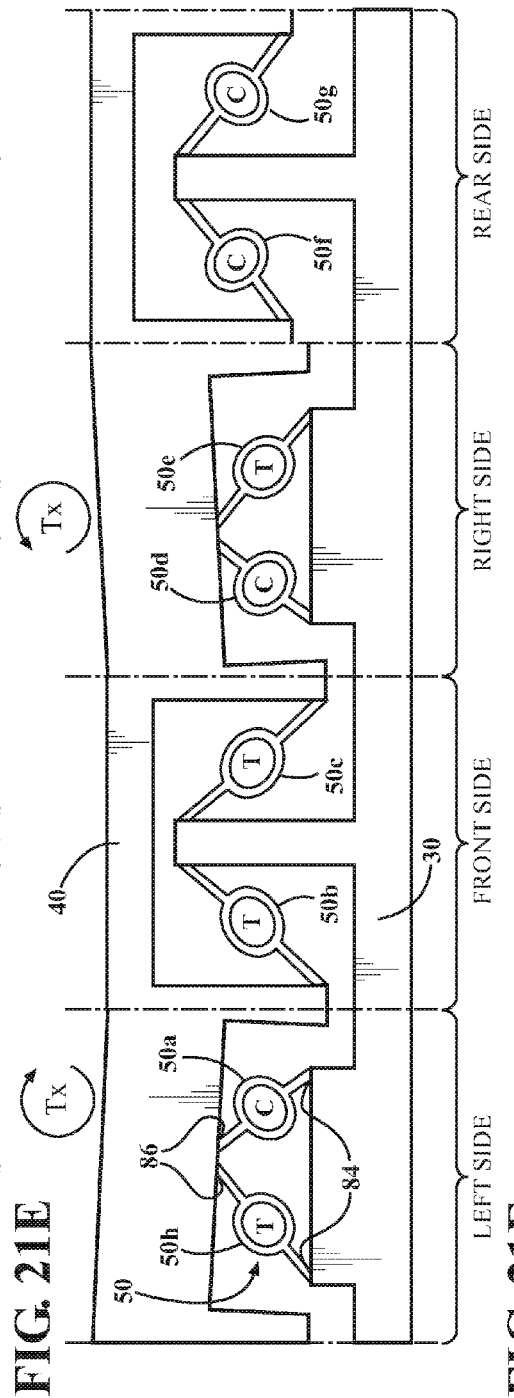
FIG. 21F is a plan view of the sides of the transducer of FIG. 20 illustrating the load cells transitioning between a rest state and a loaded state in response to an applied X-axis torque.

In FIG. 21F, an X-axis torque is applied to the second member 40. All sides of the transducer 20 experience the X-axis torque. Half of the load cells 50 go into compression and half go into tension. Specifically, load cells 50a, 50d, 50f, 50g go into compression and load cells 50b, 50c, 50e, 50h go into tension. The magnitude of the compression is the same for load cells 50a, 50d, 50f, 50g. The magnitude of tension is the same for load cells 50b, 50c, 50e, 50h. The magnitude of compression is different than the magnitude of tension. This is consistent with the matrix M showing all values being non-zero with half values being positive and half being negative in the row corresponding to T.

In FIG. 21G, a Y-axis torque is applied to the second member 40. All sides of the transducer 20 experience the Y-axis torque. Half of the load cells 50 go into compression and half go into tension. Specifically, load cells 50b, 50d, 50e, 50g go into compression and load cells 50a, 50c, 50f, 50h go into tension. The magnitude of the compression for load cells 50d, 50e is different than the magnitude of compression for load cells 50b, 50g. The magnitude of tension for load cells 50a, 50h is different than the magnitude of tension for load cells 50c, 50f. This is consistent with the matrix M showing all values being non-zero with half values being positive and half being negative in the row corresponding to $T_y$.

In FIG. 21H, a Z-axis torque is applied to the second member 40. All sides of the transducer 20 experience the Z-axis torque. Half of the load cells 50 go into compression and half go into tension. Specifically, load cells 50b, 50d, 50f, 50h go into compression and load cells 50a, 50c, 50e, 50g go into tension. The magnitude of compression is the same as the magnitude of tension. This is consistent with the matrix M showing all values having the same absolute value with half values being positive and half being negative in the row corresponding to $T_z$.

In the force/torque transducer 20 of FIG. 20, half of the load cells 50 are arranged according to a first orientation and the other half of the load cells 50 are arranged according to a second orientation that is different than the first orientation. The force/torque transducer 20 has load cells 50 having a hoop configuration. As described, each load cell 50 connects to the first member 30 at the first interface 84 and to the second member 40 at the second interface 86. The positioning of these interfaces 84, 86 determines the orientation of the load cells 50. Mainly, the positioning of these interfaces 84, 86 determines whether the load cell 50 compresses or tenses in response to a given load.

To illustrate, referring to FIGS. 21A and 21B, half of the load cells 50 have the first interface 84 positioned higher than the second interface 86. In other words, for these load cells 50, the connection to the first member 30 is higher than the connection to the second member 40. These load cells 50 are arranged, for example, according to the first orientation. The other half of the load cells 50 have the first interface 84 positioned lower than the second interface 86. In other words, for these load cells 50, the connection to the first member 30 is lower than the connection to the second member 40. In this same example, these load cells 50 are arranged according to the second orientation. The first and second orientations may be defined according to various other configurations. Additionally, the interfaces 84, 86 may be defined differently depending on the configuration.

IV. Other Embodiments

Additional embodiments of the force/torque transducer 20 are illustrated in FIGS. 20 and 22-31 and described herein wherein like numerals indicate like or corresponding parts throughout the several views.

The first and second members 30, 40 of the force/torque transducer 20 may have various configurations. In some embodiments, as shown in at least FIGS. 25, 28, 29 and 30 the first and second members 30, 40 have a geometry being substantially identical to one another. In such embodiments, the first and second members 30, 40 are generally inverted from each other such that portions of the first member 30 fit into portions of the second member 40, and vice versa. Alternatively, as shown in at least FIGS. 20, 22-24, 26, 27 and 31 the first and second members 30, 40 have a geometry being different than one another.

As shown throughout, the first member 30 has at least one side 71 and the second member 40 has at least one side 72. Each of the sides 71, 72 has at least one of the load cells 50 or interfaces with at least one of the load cells 50. In some embodiments, each of the sides 71, 72 may interface with two or more load cells 50.

Figure 22:
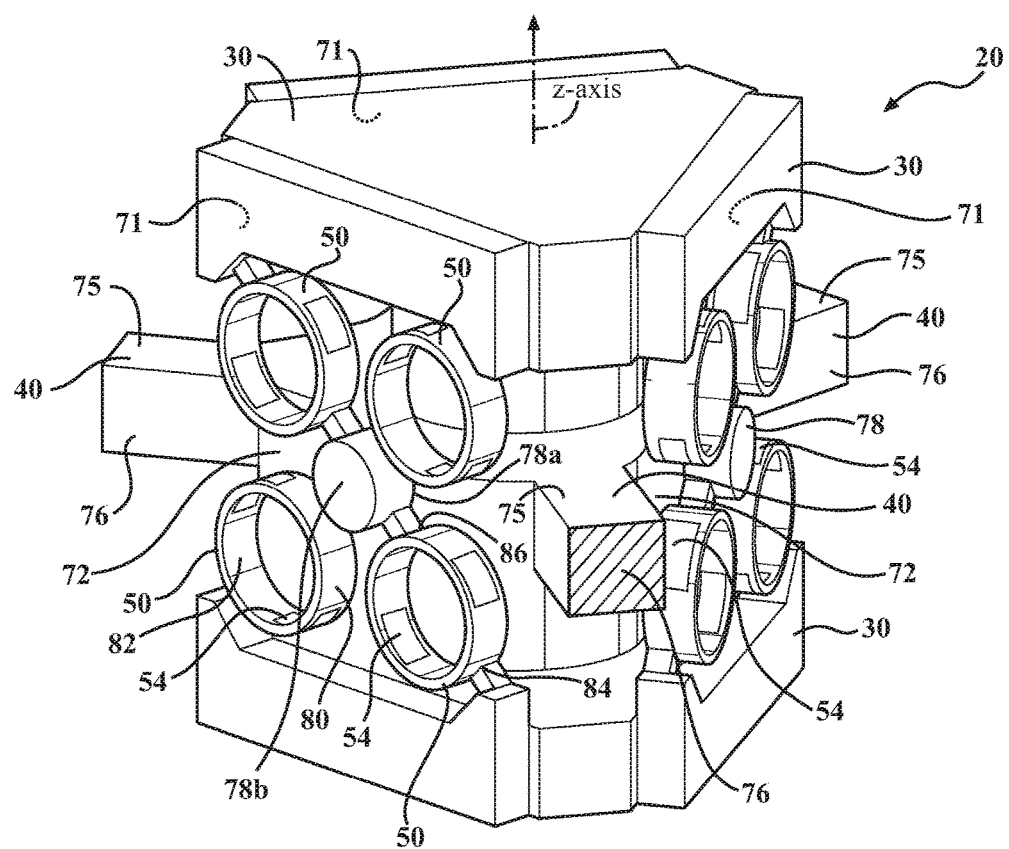
FIG. 22 is a perspective view of another embodiment of the force/torque transducer.
Figure 23:
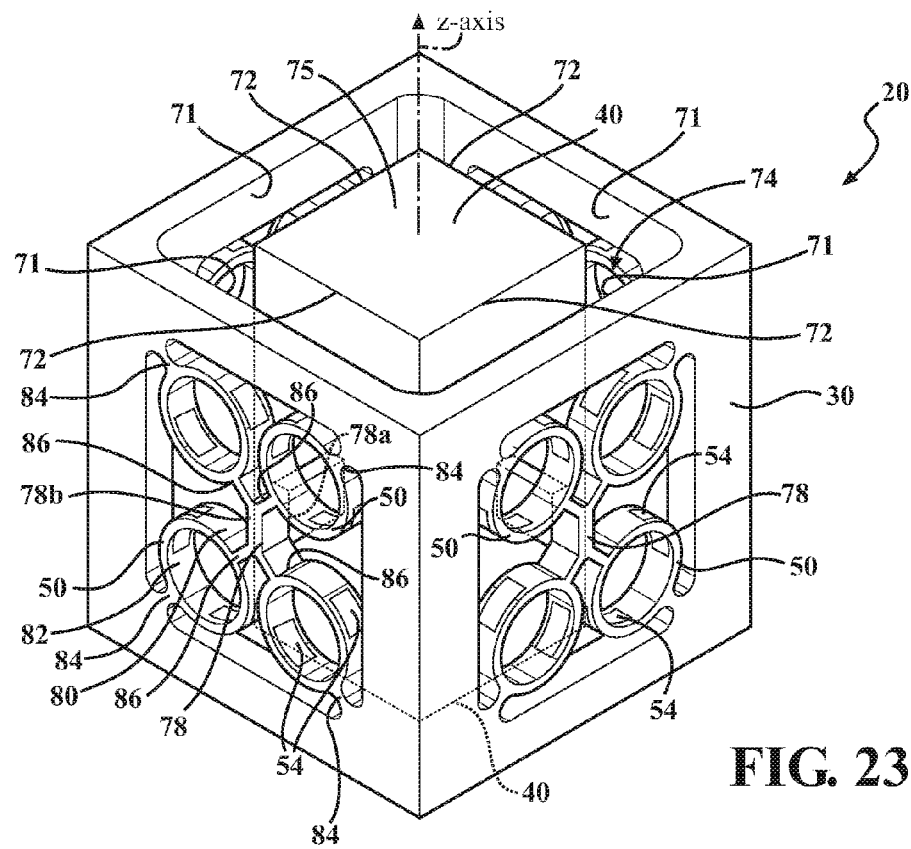
FIG. 23 is a perspective view, partially in phantom, of yet another embodiment of the force/torque transducer.
Figure 24:
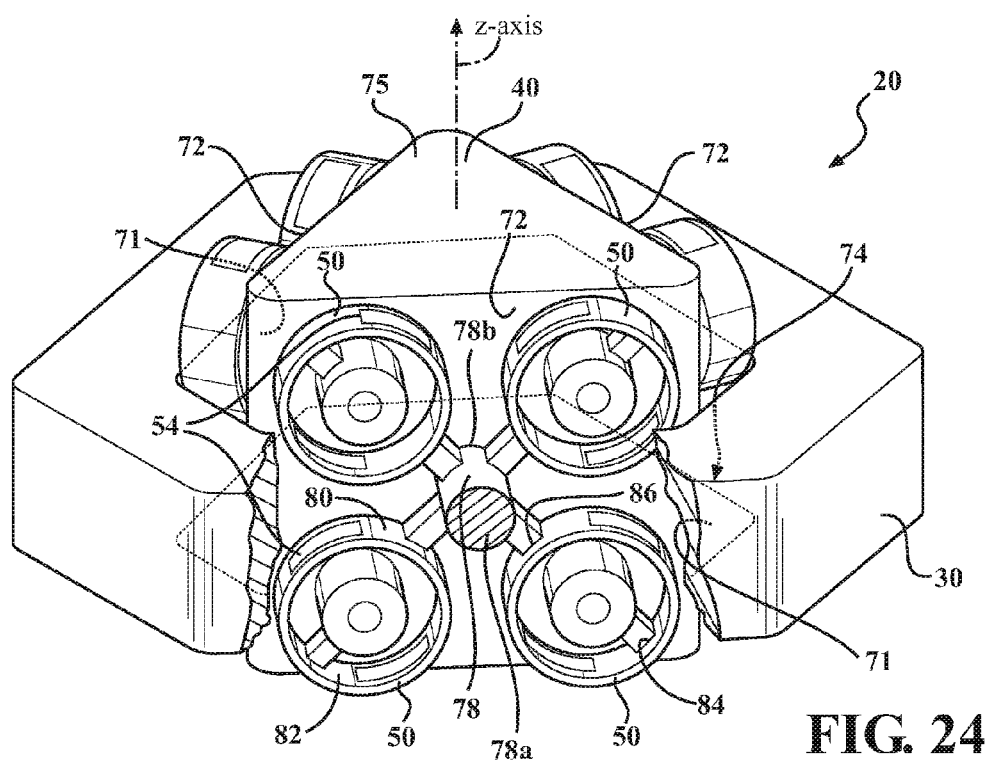
FIG. 24 is a perspective view, partially in cross-section, of yet another embodiment of the force/torque transducer.
Figure 25:
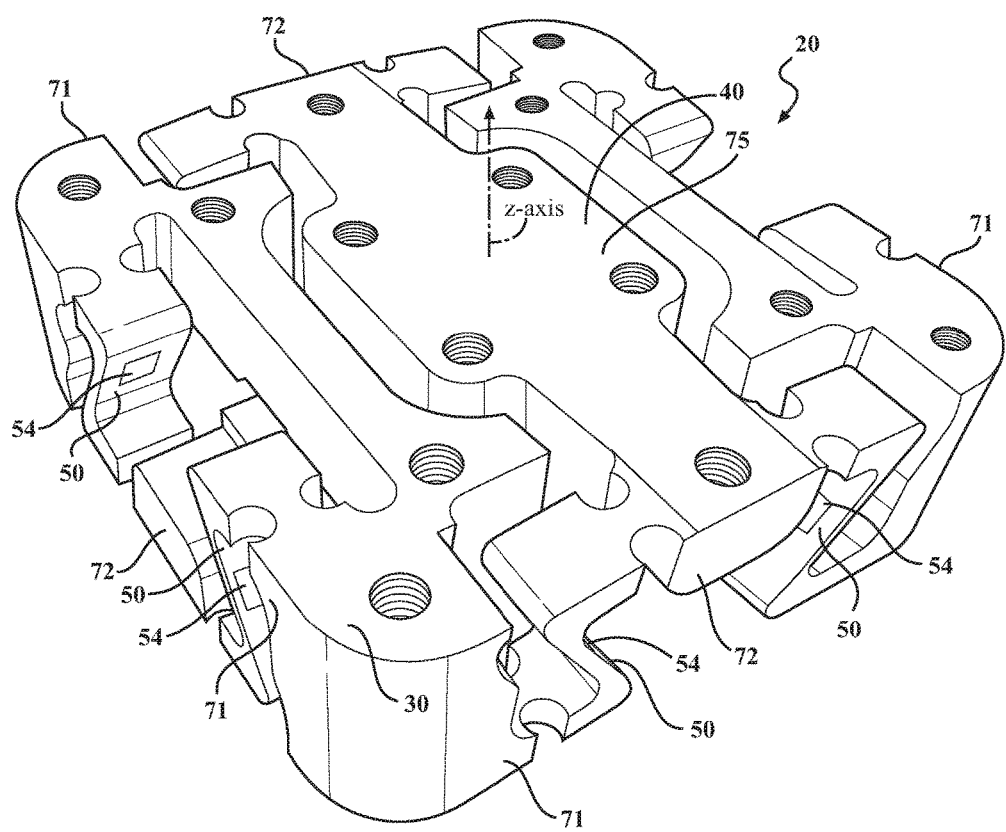
FIG. 25 is a perspective view of another embodiment of the force/torque transducer.
Figure 26:
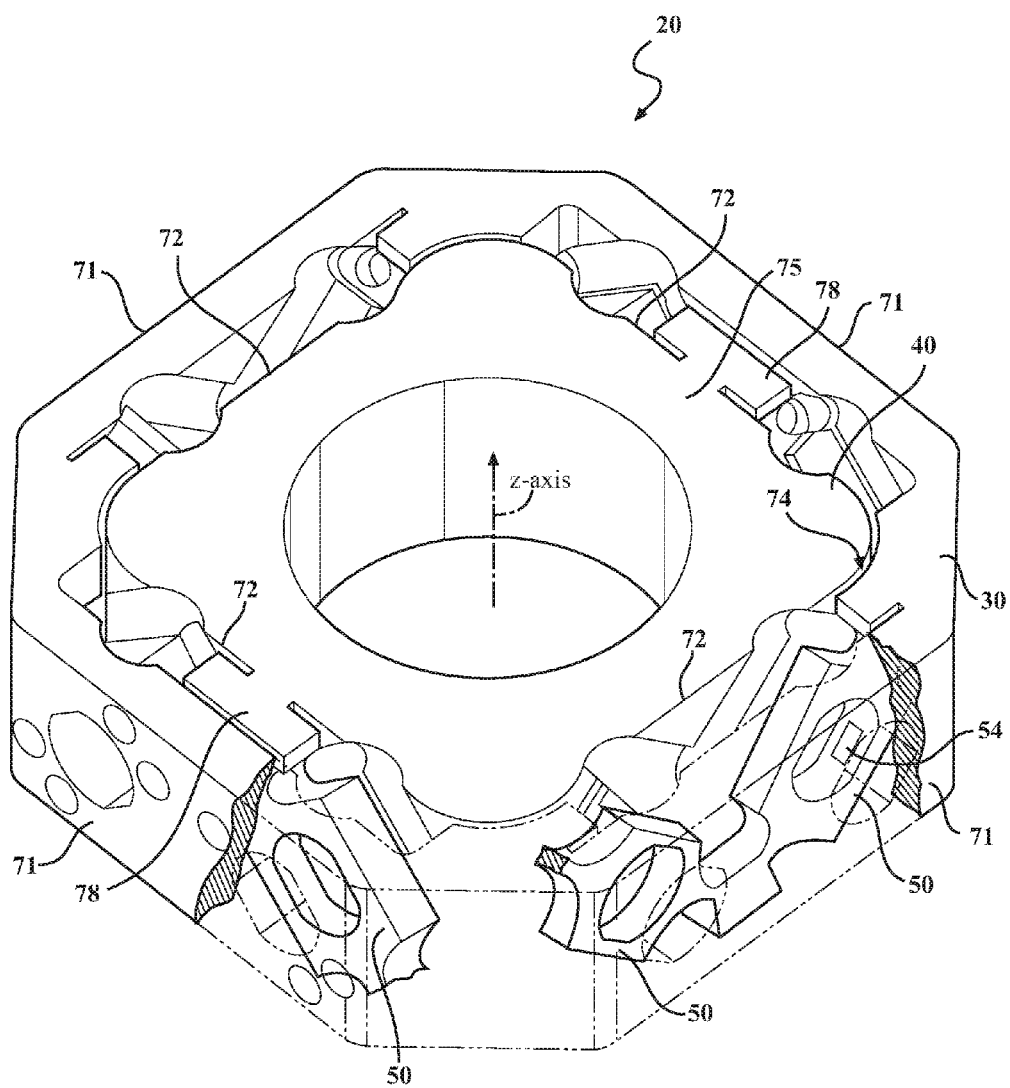
FIG. 26 is a perspective view, partially in cross-section, of yet another embodiment of the force/torque transducer.
Figure 27:
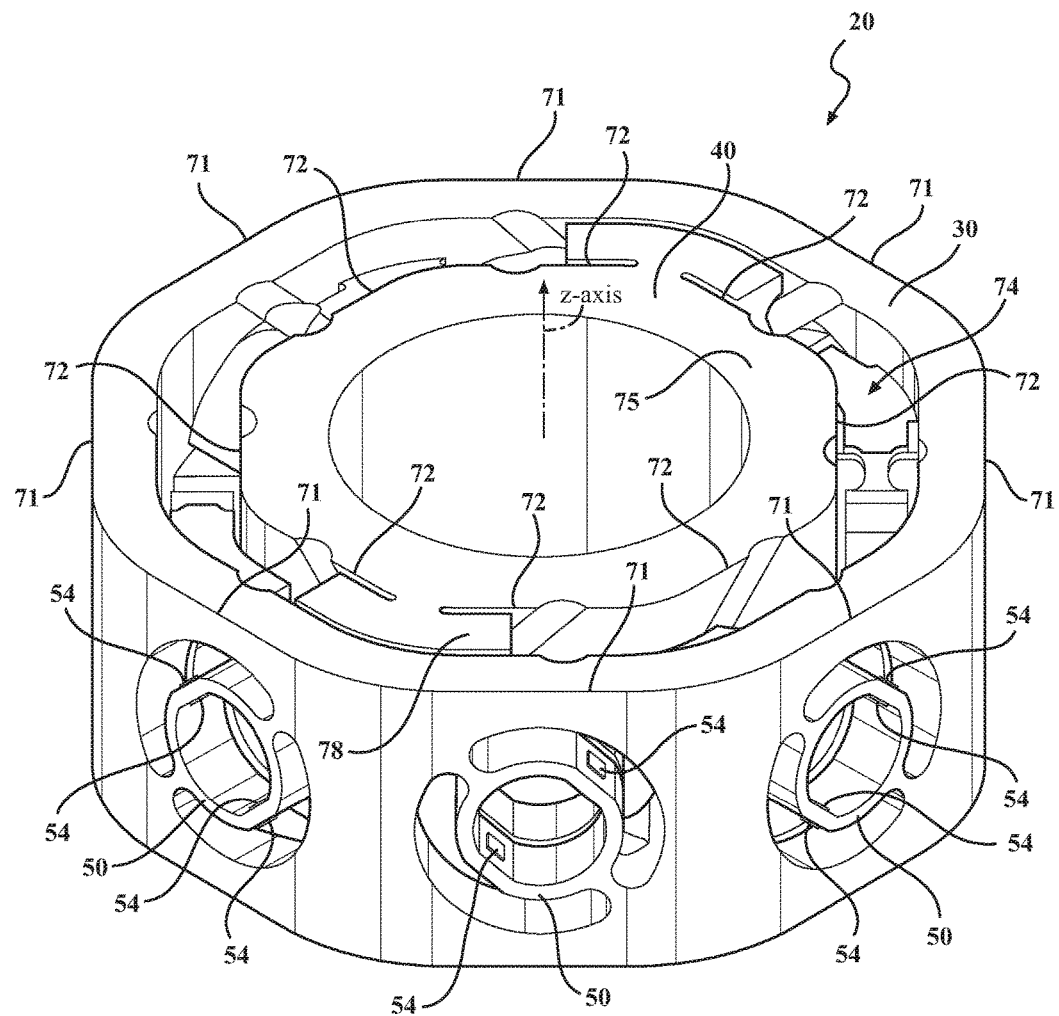
FIG. 27 is a perspective view of another embodiment of the force/torque transducer.

The first and second members 30, 40 may have any suitable number of sides 71, 72. For example, the first and second members 30, 40 may each have one side 71, 72. In such embodiments, the first and second members 30, 40 each may have a circular configuration. Alternatively, the first and second members 30, 40 may each have a plurality of sides 71, 72. In FIGS. 20, 23, 25, 26, and 29 the first and second members 30, 40 each have four sides 71, 72. In FIGS. 22 and 24, the first and second members 30, 40 each have three sides 71, 72. In FIGS. 27, 28, 30 and 31 the first and second members 30, 40 each have eight sides 71, 72. In some embodiments, any of the first and second members 30, 40 may each have one side 71, 72. For example, the sides 71, 72 may have a circular configuration.

Each of the sides 71, 72 may be an interior or exterior face. Exterior faces are disposed at an exterior of the force/torque transducer 20 such that the face could easily be contact by a human hand picking up the force/torque transducer 20 on the sides 71, 72. On the other hand, interior faces are disposed within an interior of the force/torque transducer 20 and obscured by an exterior face such that a human hand picking up the force/torque transducer 20 on the sides 71, 72, generally does not contact the interior face. In at least FIGS. 20, 25, 28, 29 and 30 each of the sides 71, 72 are exterior faces. In at least FIG. 24, the three sides 71 of the first member 30 are interior faces of the first member 30. On the other hand, the three sides 72 of the second member 40, which interface with the load cells 50, are exterior faces of the second member 40. Any of the sides 71, 72 may be interior or exterior faces. Moreover, for any given embodiment, some of the sides 71, 72 may be interior faces while other sides 71, 72 may be exterior faces.

As shown in some of the embodiments, such as shown in at least FIGS. 20, 23, 25, and 27-30, for example, the first and second members 30, 40 have an equivalent number of sides 71, 72. Alternatively, the first member 30 and the second member 40 may have a different number of sides 71, 72. The first or second member 30, 40 may have an odd number of sides 71, 72. Alternatively, the first or second member 30, 40 may have an even number of sides 71, 72.

The sides 71 of the first member 30 may align with or correspond to the sides 72 of the second member 40 to define a common side of the force/torque transducer 20. Having the sides 71, 72 correspond with one another allows easy interface between the first and second members 30, 40 and the load cells 50. In one example, as shown in at least FIGS. 20 and 25, the sides 71, 72 of the first and second members 30, 40 line up substantially flush to define the common side of the force/torque transducer 20. In some instances, the first and second sides 71, 72 may define the common side using a tongue and groove configuration, although other configurations may be possible. In at least FIG. 20, the sides 71, 72 of the first and second members 30, 40 may further correspond because an interior profile 69 of the first member 30 directly faces an interior profile 73 of the second member 40. In FIG. 20, the load cells 50 couple between the interior profiles 69, 73 of the first and second members 30, 40. The sides 71, 72 of the first and second members 30, 40 may correspond in other suitable ways.

The first and second members 30, 40 may be formed from a single unitary piece. In such instances, the first and second members 30, 40 may remain connected to one another during and after formation. Alternatively, the first and second members 30, 40 may be formed from separate pieces. The first and second members 30, 40 may be formed of the same material. On the other hand, the first and second members 30, 40 may be formed of different material.

In one embodiment, as shown in at least FIGS. 23, 24, 26, 27 and 31, the first member 30 defines a cavity 74 and the second member 40 is disposed within the cavity 74 such that the second member 40 is disposed within the first member 30. In some instances, the first member 30 surrounds a substantial majority or an entirety of the second member 40.

Alternatively, the second member 40 may define the cavity 74 and the first member 30 may be disposed within the cavity 74. In such instances, the first member 30 is disposed within the second member 40 and the second member 40 surrounds the first member 30.

In another embodiment, as shown in at least FIG. 20, for example, the first and second members 30, 40 collectively define the cavity 74. In FIG. 20, the first and second members 30, 40 jointly surround the cavity 74. In other embodiments, such as in FIGS. 12, 25, 28, 29, 30 some portions of the first member 30 may fit into the second member 40, and vice-versa, such that these portions collectively form the sides 71, 72 surrounding the cavity 74. Such embodiments may result from forming the first and second members 30, 40 from a single unitary piece or by forming the first and second members 30, 40 with substantially identical geometries.

As described, the second member 40 of the force/torque transducer 20 receives the load. The second member 40 may have any suitable configuration to receive the load. In one embodiment, the second member 40 includes at least one surface 75 for receiving the load. In other words, the load applies to the surface 75 of the second member 40. The load may be applied to the surface 75 in any suitable manner and the surface 75 may have any suitable configuration. For example, the surface 75 may be a major upper or lower face of the second member 40. The first member 30 also may surround the surface 75. In some examples, such as is shown in FIG. 22, the second member 40 has a plurality of surfaces 75 each configured to receive the load collectively or individually. Each surface 75 may be defined by a separate part of the second member 40. For example, in at least FIG. 22, the second member 40 defines a plurality of arms 76 extending beyond the first member 30. Each arm 76 defines one of the surfaces 75 for receiving the load.

The load cells 50 of the force/torque transducer 20 may have any suitable configuration. The load cells 50 are generally mechanically disposed between the first and second members 30, 40. As shown in at least FIGS. 20, 25, 29 and 30 the load cells 50 are the primary source of connection between the first and second members 30, 40. In such instances, the load cells 50 may be disposed directly between the first and second members 30, 40. In some embodiments, the load cells 50 may be the sole source of connection between the first and second members 30, 40.

Alternatively, in other embodiments, as shown in at least FIGS. 22-24, 26-28 and 31 the load cells 50 connect the first and second members 30, 40 with the aide of at least one support member 78. The support member 78 may have any suitable geometrical configuration, such as a cylinder, half cylinder or prism configuration, and the like. The support member 78 may be part of the first member 30 or second member 40. In one example, referring to at least FIG. 22, the support member 78 has first and second surfaces 78a, 78b. The support member 78 may directly connect to the first member 30 or second member 40 at the first surface 78a. The support member 78 may couple to at least one load cell 50 at the second surface 78b. In some instances, the first and second surfaces 78a, 78b may be opposing surfaces. The support member 78 is useful where several load cells 50 are grouped on each transducer side. For example, in FIGS. 22-24, the support member 78 connects to an interface between a group of four load cells 50 at each of the transducer sides. However, the support member 78 may be useful where only one or two load cells 50 are provided at each transducer side.

The force/torque transducer 20 may have any suitable number of load cells 50. In one embodiment, the force/torque transducer 20 has an even number of load cells 50. For example, in FIGS. 20 and 25-31 the force/torque transducer 20 has eight total load cells 50. In FIGS. 22 and 24 the force/torque transducer 20 has twelve total load cells 50. In FIG. 23, the force/torque transducer 20 has sixteen total load cells 50. Alternatively, the force/torque transducer 20 may have an odd number of load cells 50.

The load cells 50 generally connect the first and second members 30, 40 at the transducer side(s). The load cells 50 may be grouped at each transducer side. In one example, an even number of load cells 50 connect the first and second members 30, 40 at each transducer side. For example, in FIGS. 20, 25, 26 and 29, two load cells 50 are located at each transducer side. In FIGS. 22-24, four load cells 50 are located at each transducer side.

Alternatively, an odd number of load cells 50 connect the first and second members 30, 40 at each transducer side. For example, in FIGS. 27, 28, 30 and 31, one load cell 50 is located at each transducer side.

In some instances, at least one of the load cells 50 may be formed by a plurality of deforming members. For example, as shown in at least FIGS. 22-24, each transducer side has four hoops. However, these four hoops collectively operate as two load cells 50. Specifically, each diagonal pair of hoops forms one of the single axis load cells 50. Thus, in FIGS. 22-24 two load cells 50 are effectively located at each transducer side. Thus, in FIGS. 22 and 24, the force/torque transducer 20 effectively has six load cells 50. In FIG. 23, the force/torque transducer 20 effectively has eight load cells 50. Other single axis load cells 50 may be formed according to any suitable configuration including any suitable number of deforming members.

The load cells 50 may be components that are separately attached to the first and/or second members 30, 40. Alternatively, the load cells 50 may be machined from the same single unitary piece as the first and/or second members 30, 40.

Each load cell 50 may be made of any suitable material and may have any suitable configuration for allowing both compression and tension deformation.

In FIGS. 20 and 22-24, and 26-31 for example, each load cell 50 has the ring or hoop configuration. Alternatively, each load cell 50 may have a beam configuration, such an S-beam or Z-beam configuration (shown in FIG. 25) having a unitary middle beam that deforms in response to loads applied to the second member 40. The S-beam or Z-beam configuration is a single axis load cell. In other embodiments, each load cell 50 has a coil spring or leaf spring configuration. The load cells 50 may have other configurations not described herein. Additionally, some load cells 50 in the force/torque transducer 20 may have one configuration while other load cells 50 in the force/torque transducer 20 have another configuration.

Figure 28:
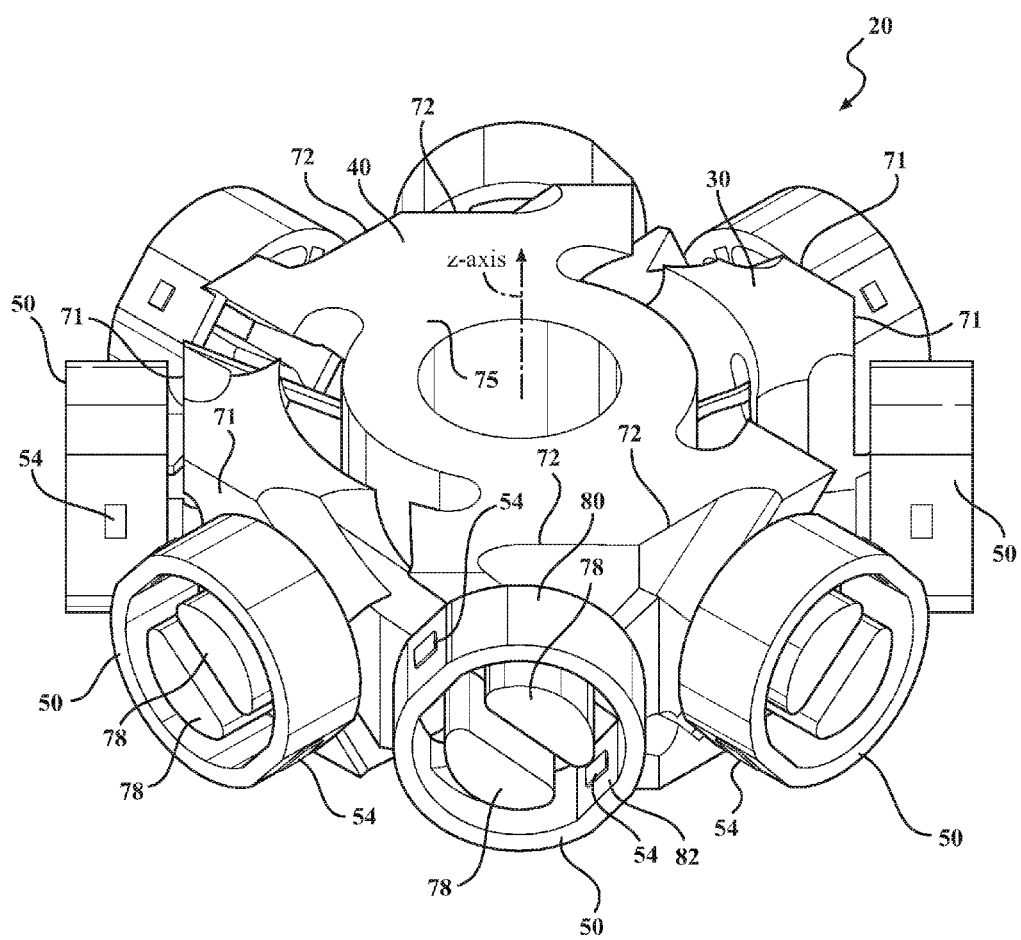
FIG. 28 is a perspective view of another embodiment of the force/torque transducer.
Figure 29:
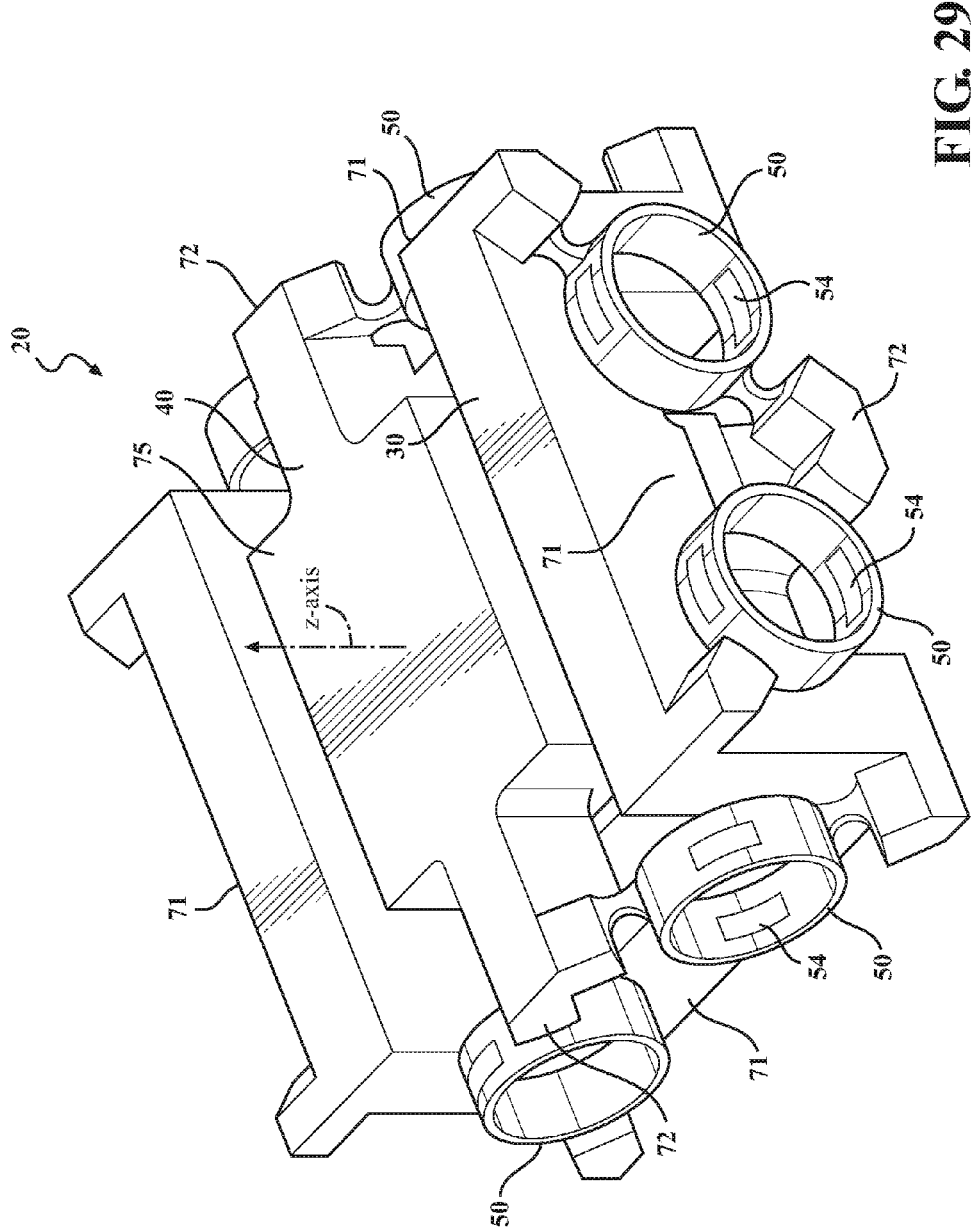
FIG. 29 is a perspective view of another embodiment of the force/torque transducer.
Figure 30:
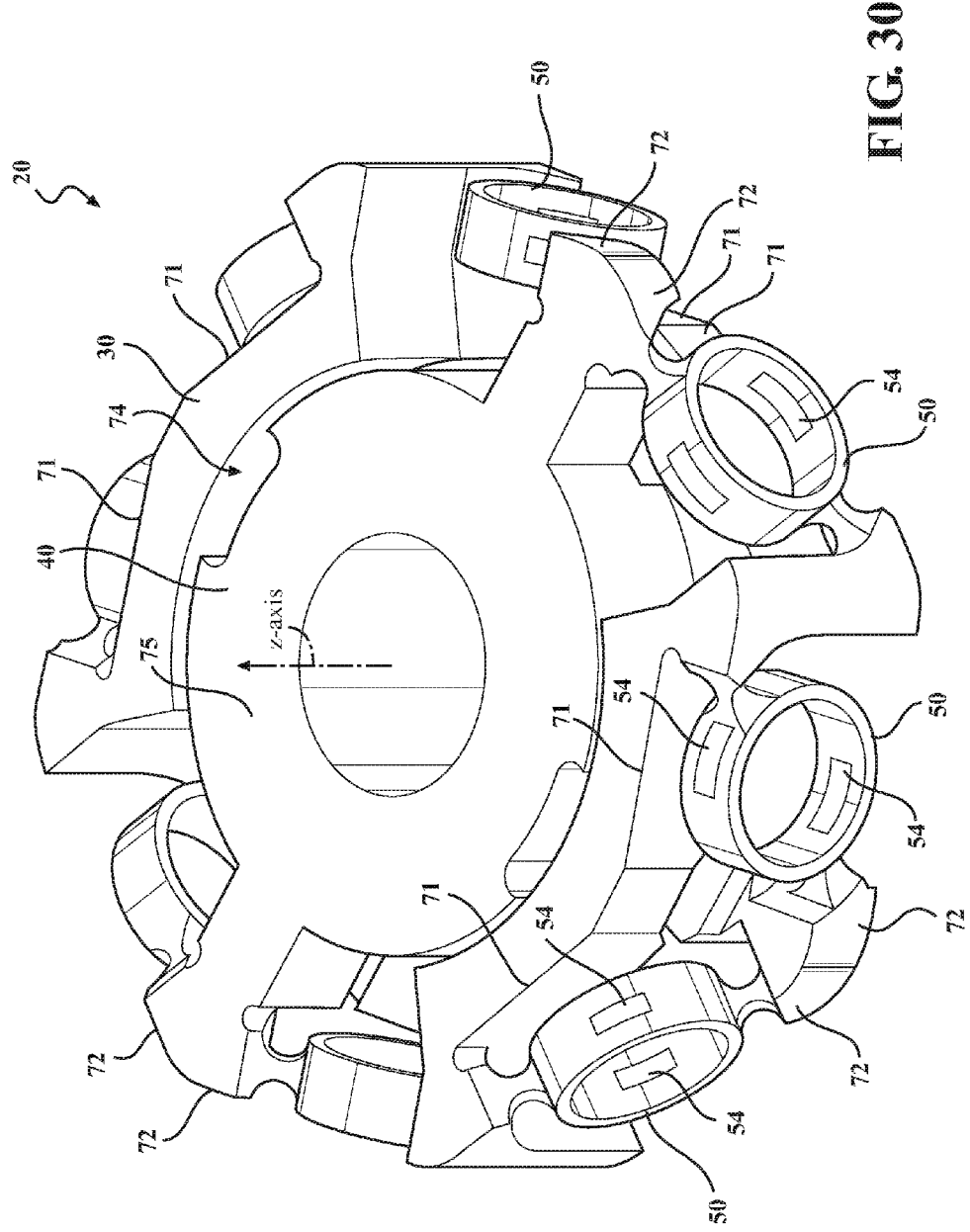
FIG. 30 is a perspective view of another embodiment of the force/torque transducer.
Figure 31:
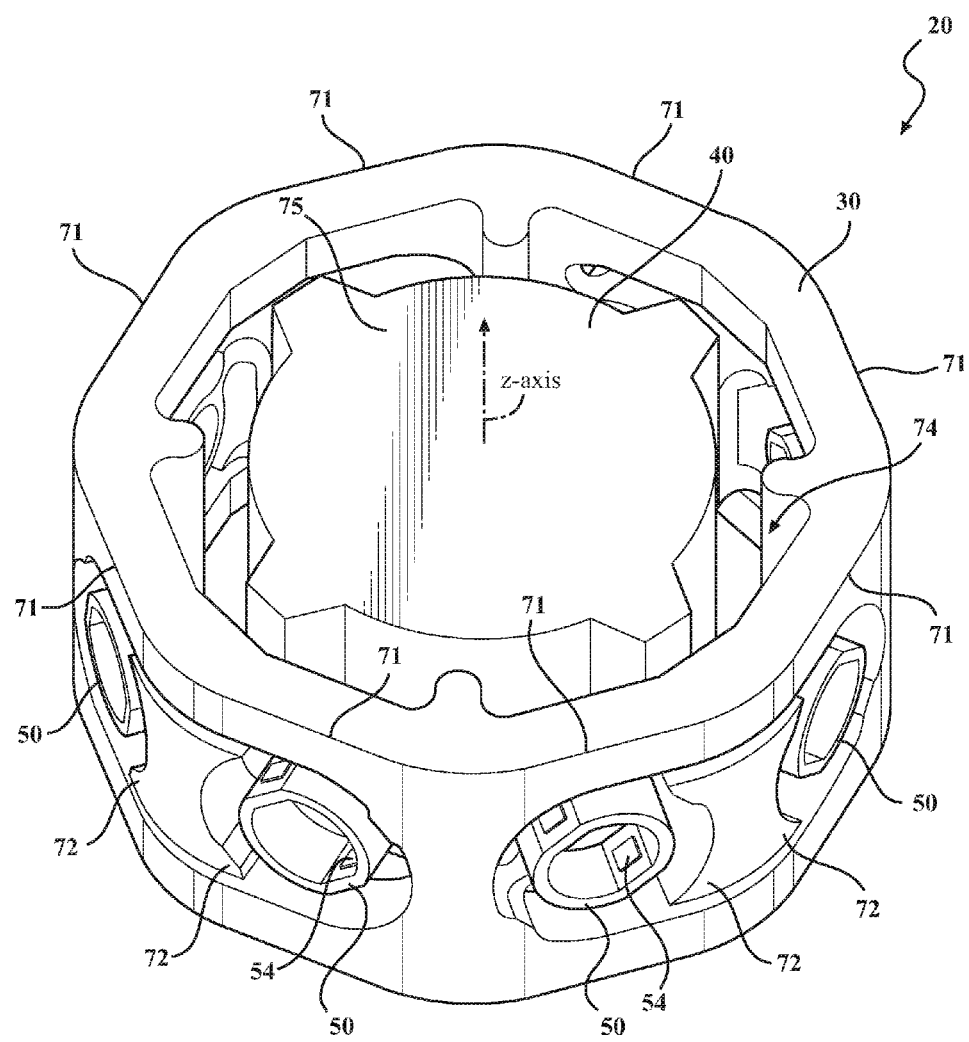
FIG. 31 is a perspective view of yet another embodiment of the force/torque transducer.

In some instances, such as shown in FIGS. 20 and 22-23, 26, 27, and 29-31 the outer surface 80 of the load cell 50 connects to the first or second member 30, 40. Alternatively, as shown in FIGS. 24 and 28 the inner surface 82 of the load cell 50 connects to the first or second member 30, 40. Additionally, both outer and inner surfaces 80, 82 may connect to the first and/or second member 30, 40. Each load cell 50 may have a plurality of outer surfaces 80 and a plurality of inner surfaces 82.

The length of the load cell 50 may be measured in various ways. For coil, s-beam, and/or z-beam configurations, the first interface 84 may be one end of the coil, s-beam, or z-beam and the second interface 86 is the opposing end of the coil, s-beam, or z-beam. In such instances, the length is measured between the opposing ends. Compression of the load cell 50 may occur in ways other than a shortening of length from equilibrium. Similarly, tensioning of the load cell 50 may occur in ways other than an expansion of length from equilibrium.

In some embodiments, half of the load cells 50 go into compression and the other half of the load cells 50 go into tension for all loads applied to the second member 40. Said differently, for every instance that the second member 40 axially and/or rotationally displaces relative to the first member 30 with respect to each of the X, Y, and Z-axes, half of the load cells 50 go into compression and the other half of the load cells 50 go into tension. The load cells 50 from among the half going into compression or tension may be different depending on the load applied.

In some cases, the load cells 50 at a first pair of opposing transducer sides (such as the front and rear sides) are configured to go into compression and the load cells 50 at a second pair of opposing transducer sides (such as the right and left sides) are configured to go into tension for loads applied to the second member 40, such as loads applied along the Z-axis.

In other cases, half of the load cells 50 at each of the transducer sides go into compression and the other half of the load cells 50 at each of the transducer sides go into tension for loads applied to the second member 40. For example, suppose the force/torque transducer 20 has four transducer sides with two load cells 50 connecting the first and second members 30, 40 at each transducer side. In this embodiment, one of the load cells 50 at each of the four transducer sides is configured to go into compression for all X, Y, and Z-axis loads. Meanwhile, the remaining load cell 50 at each of the four transducer sides is configured to go into tension for all X, Y, and Z-axis loads. With an even number of load cells 50, this embodiment is possible for force/torque transducers 20 having any number of transducer sides.

In some embodiments, half of the load cells 50 at each of the transducer sides are arranged according to the first orientation and the other half of the load cells 50 at each of the transducer sides are arranged according to the second orientation. To illustrate, in FIG. 23 the force/torque transducer 20 has four identically configured transducer sides. At each of the transducer sides there are two load cells 50, with each single axis load cell 50 defined by opposing diagonal pairs of hoops. When each transducer side is viewed from a front view, one of the load cells 50 has the first interface 84 diagonally connecting to the first member 30 at opposing lower-left and upper-right corners. This same load cell 50 has the second interface 86 connecting to the second member 40 by diagonally interfacing with lower-left and upper-right corners of the support member 78. This first load cell 50 on each of the transducer sides is arranged according to the first orientation. To the contrary, the other load cell 50 at each of the transducer sides has the first interface 84 diagonally connecting to the first member 30 at opposing lower-right and upper-left corners. This same load cell 50 has the second interface 86 connecting to the second member 40 by diagonally interfacing with lower right and upper-left corners of the support member 78. This second load cell 50 at each of the transducer sides is arranged according to the second orientation.

In another embodiment, a first group of load cells 50 at a first transducer side is oriented identically to a second group of load cells 50 at a second, opposing transducer side. A third group of load cells 50 at a third transducer side may also be oriented identically to a fourth group of load cells 50 at a fourth, opposing transducer side. In this embodiment, the individual load cells 50 in each group may be oriented differently or the same. To illustrate, for example, the force/torque transducer 20 in at least FIGS. 20, 25, 26 and 29 have opposing front and back transducer sides and opposing left and right transducer sides. The individual load cells 50 on the front side have different orientations. However, as a group, the load cells 50 on the opposing back side are oriented identically to the load cells 50 on the front side. That is, the individual load cells 50 on the back side have different orientations, but as a group they are identical to the load cells 50 on the front side.

The configuration described above may also be implemented where the force/torque transducer 20 has more than four transducer sides. For example, as shown in at least FIGS. 27, 28 and 31, which have eight transducer sides, the opposing pairs of load cells 50 can be conceptually grouped using adjacent pairs of sides, rather than single sides. That is, a first group of load cells 50 at a first pair of transducer sides is oriented identically to a second group of load cells 50 at a second, opposing pair transducer sides.

Another embodiment is possible where each group of load cells 50 at each transducer side may be oriented identically. For example, in FIGS. 22-24, each group of load cells 50 on each transducer side are oriented identically.

Advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A force/torque transducer comprising:
a first member;
a second member configured to receive a load; and
a first load cell and a second load cell each connecting the first and second members;
the first load cell including a first sensor configured to generate a first sensor measurement responsive to physical deformation of the first load cell;
the second load cell including a second sensor configured to generate a second sensor measurement responsive to physical deformation of the second load cell;
the first sensor measurement convertible into a force/torque measurement for the first load cell when the first sensor measurement is multiplied by a first value of a transformation matrix, with the first value having an algebraic sign being positive or negative;
the second sensor measurement convertible into a force/torque measurement for the second load cell when the second sensor measurement is multiplied by a second value of the transformation matrix, with the second value having an algebraic sign being opposite the algebraic sign of the first value;
the first and second load cells are geometrically arranged relative to the first and second members and relative to each other such that, in response to the force/torque transducer experiencing systematic drift, the first and second load cells are configured to either both go into compression or to both go into tension and with physical deformation of the first and second load cells resulting from compression or tension causing the first and second sensors to generate first and second sensor measurements having the same algebraic sign; and
the first and second sensor measurements resulting from systematic drift and having the same algebraic sign are convertible by the first and second values of the transformation matrix having opposite algebraic signs to produce force/torque measurements for the first and second load cells that are opposite algebraic signs such that the force/torque measurements of the first and second load cells resulting from systematic drift are offset when summed.

2. The force/torque transducer of claim 1 wherein:
the first and second values of the transformation matrix have equal absolute values; and
the first and second sensor measurements resulting from systematic drift have equal absolute values such that the force/torque measurements of the first and second load cells resulting from systematic drift are completely offset when summed.

3. The force/torque transducer of claim 1 wherein:
the first and second values of the transformation matrix have equal absolute values; and
the first and second sensor measurements resulting from systematic drift have substantially equal absolute values such that the force/torque measurements of the first and second load cells resulting from systematic drift are substantially offset when summed.

4. The force/torque transducer of claim 1 wherein the first and second load cells are geometrically arranged relative to the first and second members and relative to each other such that, in response to application of the load:
the first load cell is configured to go into compression and with physical deformation of the first load cell resulting from compression causing the first sensor to generate the first sensor measurement having an algebraic sign being positive or negative;
the second load cell is configured to go into tension and with physical deformation of the second load cell resulting from tension causing the second sensor to generate the second sensor measurement having an algebraic sign being opposite the algebraic sign of the first sensor measurement; and
the first and second sensor measurements resulting from application of the load and having opposite algebraic signs are convertible by the first and second values of the transformation matrix having opposite algebraic signs to produce force/torque measurements for the first and second load cells that are the same algebraic sign such that the force/torque measurements of the first and second load cells resulting from application of the load are positively combined when summed.

5. The force/torque transducer of claim 4 wherein:
the first and second values of the transformation matrix have equal absolute values; and
the first and second sensor measurements resulting from application of the load have equal absolute values.

6. The force/torque transducer of claim 4 wherein:
the first and second values of the transformation matrix have equal absolute values; and
the first and second sensor measurements resulting from application of the load have substantially equal absolute values.

7. The force/torque transducer of claim 4 further comprising a plurality of load cells in addition to the first and second load cells, and wherein the plurality of load cells includes an even number of load cells.

8. The force/torque transducer of claim 7 wherein the plurality load cells are geometrically arranged such that, in response to application of the load, half of the load cells are configured to go into compression and half of the load cells are configured to go into tension.

9. The force/torque transducer of claim 7 wherein the plurality load cells are geometrically arranged such that half of the load cells are arranged according to a first orientation and the other half of the load cells are arranged according to a second orientation that is different than the first orientation.

10. The force/torque transducer of claim 7 wherein the first member and the second member have an equivalent number of corresponding sides and wherein an even number of load cells connect the first and second members at each corresponding side.

11. The force/torque transducer of claim 10 wherein half of the load cells at each corresponding side are arranged according to a first orientation and the other half of the load cells at each corresponding side are arranged according to a second orientation that is different than the first orientation.

12. The force/torque transducer of claim 7 wherein each of the plurality of load cells are single-axis load cells and wherein the plurality of load cells collectively monitor six-degrees of freedom.

13. The force/torque transducer of claim 4 further comprising a plurality of load cells in addition to the first and second load cells, and wherein the plurality of load cells includes an odd number of load cells.

14. The force/torque transducer of claim 1 further comprising:
a third load cell including a third sensor configured to generate a third sensor measurement responsive to physical deformation of the third load cell;
the third sensor measurement convertible into a force/torque measurement for the third load cell when the third sensor measurement is multiplied by a third value of the transformation matrix, with the third value having an algebraic sign being opposite the algebraic sign of the first value and being the same algebraic sign as the second value, wherein the absolute value of the first value is equal to the sum of the absolute values of the second and third values;
the first, second and third load cells are geometrically arranged relative to the first and second members and relative to each other such that, in response to the force/torque transducer experiencing systematic drift, the first, second and third load cells are configured to either all go into compression or all go into tension and with physical deformation of the first, second and third load cells resulting from compression or tension causing the first, second and third sensors to generate first, second and third sensor measurements having the same algebraic sign; and
the first, second and third sensor measurements resulting from systematic drift and having the same algebraic sign are convertible by the first, second, and third values of the transformation matrix to produce a force/torque measurement for the first load cell that is of opposite algebraic sign from the force/torque measurements for the second and third load cells such that the force/torque measurement of the first load cell resulting from systematic drift offsets the force/torque measurements of the second and third load cells resulting from systematic drift when summed.

15. A robotic device comprising the force/torque transducer as defined in claim 1, wherein the force/torque transducer is connected between a manipulator and an end effector of the robotic device.

16. A method for operating a force/torque transducer to offset systematic drift experienced by the force/torque transducer, the force/torque transducer comprising a first member, a second member configured to receive a load, a first load cell and a second load cell each connecting the first and second members, the first load cell including a first sensor configured to generate a first sensor measurement responsive to physical deformation of the first load cell, and the second load cell including a second sensor configured to generate a second sensor measurement responsive to physical deformation of the second load cell, the first sensor measurement convertible into a force/torque measurement for the first load cell when the first sensor measurement is multiplied by a first value of a transformation matrix, with the first value having an algebraic sign being positive or negative, the second sensor measurement convertible into a force/torque measurement for the second load cell when the second sensor measurement is multiplied by a second value of the transformation matrix, with the second value having an algebraic sign being opposite the algebraic sign of the first value, the method comprises:
physically deforming the first and second load cells to either both go into compression or to both go into tension in response to the force/torque transducer experiencing systematic drift;
generating, with the first and second sensors, first and second sensor measurements resulting from systematic drift such that the first and second sensor measurements have the same algebraic sign;
applying the first and second sensor measurements having the same algebraic signs to the first and second values of the transformation matrix having opposite algebraic signs;
producing force/torque measurements for the first and second load cells resulting from systematic drift that are opposite algebraic signs; and
summing the force/torque measurements of the first and second load cells of opposite algebraic signs to offset systematic drift.

17. The method of claim 16 further comprising:
physically deforming the first load cell to go into compression in response to application of the load;
generating, with the first sensor, the first sensor measurement resulting from application of the load such that the first sensor measurement has an algebraic sign being positive or negative;
physically deforming the second load cell to go into tension in response to application of the load;
generating, with the second sensor, the second sensor measurement resulting from application of the load such that the second sensor measurement has an algebraic sign being opposite the algebraic sign of the first sensor measurement; and
applying the first and second sensor measurements having opposite algebraic signs to the first and second values of the transformation matrix having opposite algebraic signs;
producing force/torque measurements for the first and second load cells resulting from application of the load that are the same algebraic sign; and
summing the force/torque measurements of the first and second load cells of the same algebraic sign such that the force/torque measurements are positively combined.

18. The method of claim 16 wherein the force/torque transducer further comprises a third load cell including a third sensor configured to generate a third sensor measurement responsive to physical deformation of the third load cell, the third sensor measurement convertible into a force/torque measurement for the third load cell when the third sensor measurement is multiplied by a third value of the transformation matrix, with the third value having an algebraic sign being opposite the algebraic sign of the first value and being the same algebraic sign as the second value, wherein the absolute value of the first value is equal to the sum of the absolute values of the second and third values, the method further comprising:
physically deforming the first, second, and third load cells to all go into compression or to all go into tension in response to the force/torque transducer experiencing systematic drift;
generating, with the first, second and third sensors, first, second and third sensor measurements resulting from systematic drift such that the first, second and third sensor measurements have the same algebraic signs;

applying the first, second and third sensor measurements having the same algebraic signs to the first, second and third values of the transformation matrix;
producing the force/torque measurements for the first, second and third load cells resulting from systematic drift whereby the force/torque measurement for the first load cell is of opposite algebraic sign from the force/torque measurements for the second and third load cells; and
summing the force/torque measurements of the first, second and third load cells to offset systematic drift.

* * * * *